US010988505B2

(12) United States Patent
Boudreault et al.

(10) Patent No.: US 10,988,505 B2
(45) Date of Patent: Apr. 27, 2021

(54) MATRIPTASE INHIBITORS AND USES THEREOF

(71) Applicant: 03;SOCIÉTÉ DE COMMERCIALISATION DES PRODUITS DE LA RECHERCHE APPLIQUÉE SOCPRA SCIENCES SANTÉ ET HUMAINES S.E.C., Sherbrooke (CA)

(72) Inventors: Pierre-Luc Boudreault, Montréal (CA); Éloïc Colombo, Montréal (CA); Richard Leduc, Montréal (CA); Eric Marsault, Montréal (CA); Baptiste Plancq, Montréal (CA); Martin Richter, Montréal (CA)

(73) Assignee: SOCIÉTÉ DE COMMERCIALISATION DES PRODUITS DE LA RECHERCHE APPLIQUÉE SOCPRA SCIENCES SANTÉ ET HUMAINES S.E.C., Sherbrooke (CA)

( * ) Notice: Subject to any disclaimer, the term of this patent is extended or adjusted under 35 U.S.C. 154(b) by 0 days.

(21) Appl. No.: 16/471,979

(22) PCT Filed: Dec. 21, 2017

(86) PCT No.: PCT/CA2017/051575
§ 371 (c)(1),
(2) Date: Jun. 20, 2019

(87) PCT Pub. No.: WO2018/112648
PCT Pub. Date: Jun. 28, 2018

(65) Prior Publication Data

US 2019/0337981 A1 Nov. 7, 2019

(30) Foreign Application Priority Data

Dec. 23, 2016 (CA) ................................ CA 2953159
Dec. 23, 2016 (CA) ................................ CA 2953166
Dec. 23, 2016 (CA) ................................ CA 2953168

(51) Int. Cl.
*A61K 38/00* (2006.01)
*C07K 5/09* (2006.01)
(Continued)

(52) U.S. Cl.
CPC ............ *C07K 5/0817* (2013.01); *A61P 11/00* (2018.01); *A61P 19/02* (2018.01); *A61P 31/16* (2018.01); *C07K 5/0808* (2013.01); *A61K 38/00* (2013.01)

(58) Field of Classification Search
None
See application file for complete search history.

(56) References Cited

FOREIGN PATENT DOCUMENTS

WO 2012162828 12/2012

OTHER PUBLICATIONS

Sun et al. Molecular Medicine Reports 14: 1465-1474, 2016.*
(Continued)

*Primary Examiner* — Jeanette M Lieb
(74) *Attorney, Agent, or Firm* — Hovey Williams LLP

(57) ABSTRACT

The present application relates to a compound of formulae (I), (II) or (III) or a pharmaceutically acceptable salt thereof, methods and uses thereof for treating disorders associated with matriptase activity.

(I)

;

(II)

or (Continued)

-continued (III)

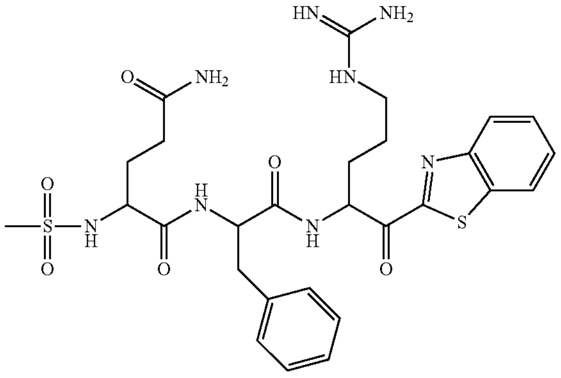

20 Claims, 1 Drawing Sheet

(51) Int. Cl.
*A61P 19/02* (2006.01)
*A61P 11/00* (2006.01)
*A61P 31/16* (2006.01)
*C07K 5/083* (2006.01)

(56) References Cited

OTHER PUBLICATIONS

National Institute of Cancer—understanding and related topics, accessed Aug. 18, 2019 at URL: https://www.cancer.gov/about-cancer/understanding/what-is-cancer.*
Enablement Decision Tree, Example F, situation 1; Aug. 2020.*
Kanemaru et al. Int. J. Cancer: 140, 130-141; 2017.*
International Search Report and Written Opinion on corresponding PCT/CA2017/051575, dated Feb. 21, 2018.
Duchene, et al., "Analysis of Subpocket Selectivity and Identification of Potent Selective Inhibitors for Matriptase and Matriptase-2", J. Med. Chem., 2014, 57, 10198-10204.
Zoratti, et al., "Targeting matriptase in breast cancer abrogates tumour progression via impairment of stromal-epithelial growth factor signalling", Nature Communications, Apr. 15, 2015.
Milner, et al., "Matriptase Is a Novel Initiator of Cartilage Matrix Degradation in Osteoarthritis", Arthritis & Rheumatism, vol. 62, No. 7, Jul. 2010, pp. 1955-1966.
Bardou, et al., "Membrane-anchored Serine Protease Matriptase Is a Trigger of Pulmonary Fibrogenesis", Am J Respir Crit Care Med, vol. 193, Iss 8, pp. 847-860, Apr. 15, 2016.

* cited by examiner

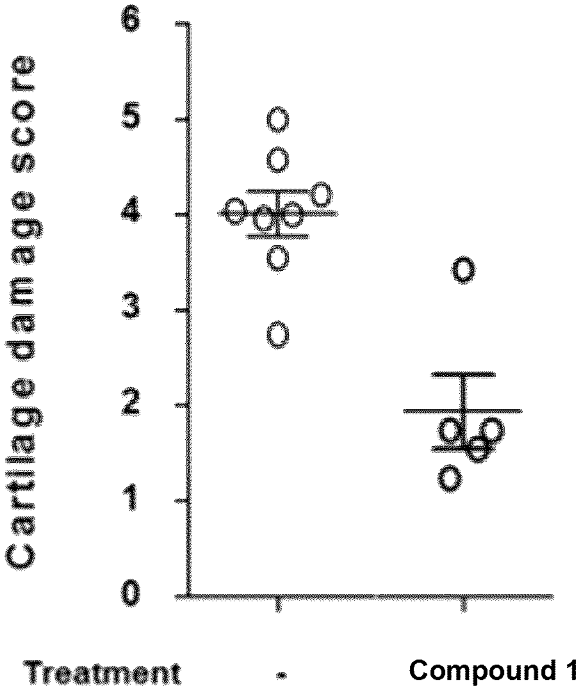
Cartilage damage score
6
5
4
3
2
1
0
Treatment
-
Compound 1

MATRIPTASE INHIBITORS AND USES THEREOF

RELATED APPLICATIONS

This application is the U.S. National Stage of International Patent Application No. PCT/CA2017/051575, filed Dec. 21, 2017, which is hereby incorporated by reference in its entirety, and which claims priority from CA 2,953,159, filed Dec. 23, 2016, CA 2,953,168, filed Dec. 23, 2016, and CA 2,853,166, filed Dec. 23, 2016, each of which are all incorporated by reference herein in their entireties.

BACKGROUND

Field of the Invention

This application relates to novels compounds, pharmaceutical compositions comprising same and uses thereof.

Description of Related Art

Matriptase is a TTSP (type II transmembrane serine protease) of about 855 amino acids that belongs to the family of 51 trypsin-like proteases. Matriptase has been reported to be implicated in several diseases such as cancer (Sales et al. Oncogene, 2015 Jan. 15; 34(3): 346-356. doi:10.1038/onc.2013.563; Zoratti et al. Nat Commun; 6: 6776. doi:10.1038/ncomms7776; Zarif et al. Oncotarget, Jan. 29, 2015; Vol. 6, No. 9:6862; Bocheva et al. Journal of Investigative Dermatology (2009) 129, 1816-1823; doi:10.1038/jid.2008.449; and Cheng et al; Histopathology 2014, 65, 24-34. DOI: 10.1111/his.12361), osteoarthritis (Milner et al. Arthritis & Rheumatism, Vol. 62, No. 7, July 2010, pp 1955-1966), atherosclerosis, pulmonary fibrosis (Bardou et al. Am J Respir Crit Care Med Vol 193, Iss 8, pp 847-860, Apr. 15, 2016) and influenza (Beaulieu et al. J. Virol. 87,4237-4251 (2013)).

WO2012/162828 describes ketobenzothiazole peptides having matriptase inhibition activity. While ketobenzothiazole peptides of WO2012/162828 are reported as inhibiting matriptase activity at the enzymatic level, the activity of a representative compound of WO2012/162828 (IN-1) when tested in a cellular assay is significantly reduced. There is therefore a need for novel matriptase inhibitors.

SUMMARY

The present description relates to compounds of formula:

(I)

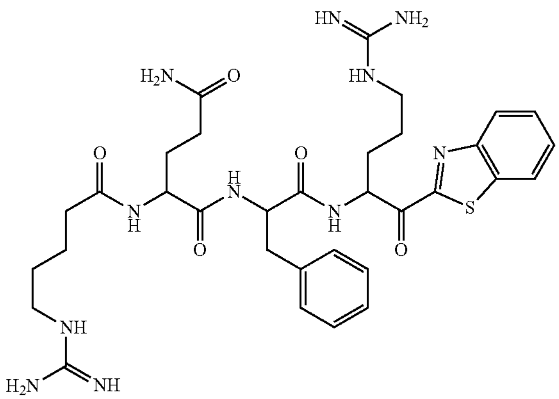 [SMILES: N=C(N)NCCCCC(=O)NC(CCC(N)=O)C(=O)NC(Cc1ccccc1)C(=O)NC(CCCNC(=N)N)C(=O)c1nc2ccccc2s1]

;

-continued (II)

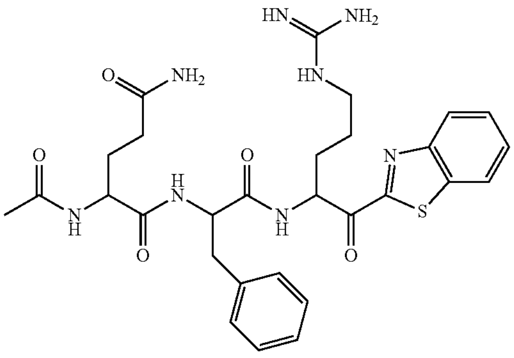

or (III)

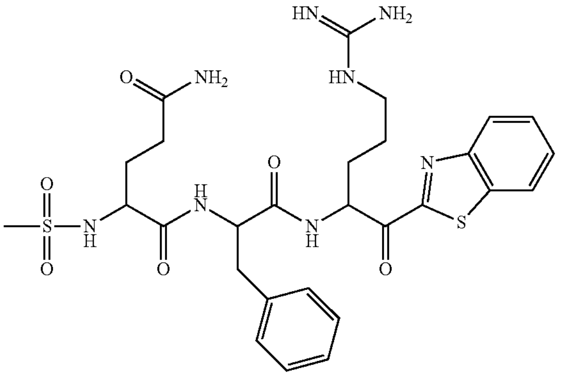

or a pharmaceutically acceptable salt thereof.

According to one aspect, there is provided a compound of formula:

Ia

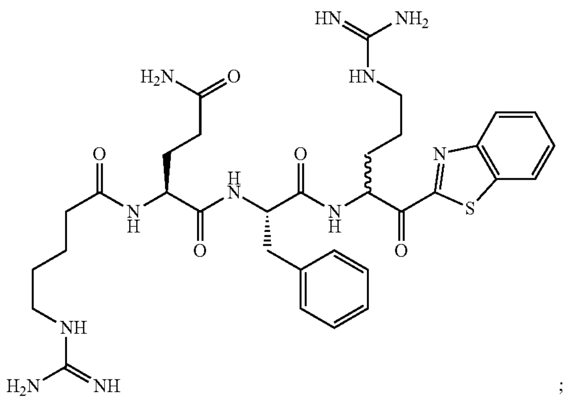

;

-continued
Ib
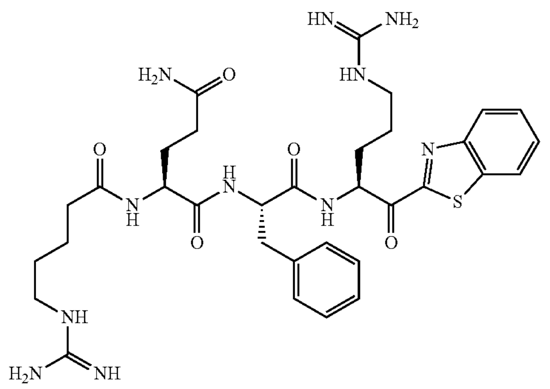 [SMILES: N=C(N)NCCCCC(=O)N[C@@H](CCC(N)=O)C(=O)N[C@@H](Cc1ccccc1)C(=O)N[C@@H](CCCNC(=N)N)C(=O)c1nc2ccccc2s1]
or
Ic
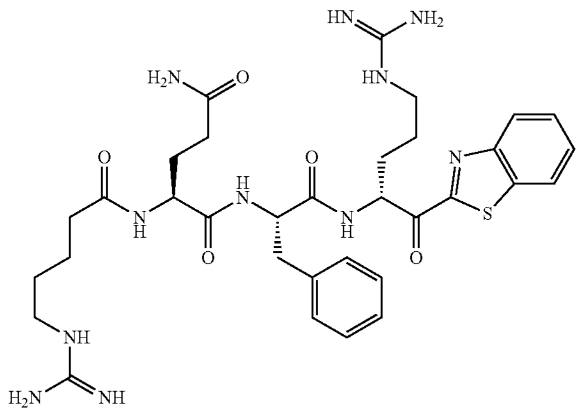
IIa
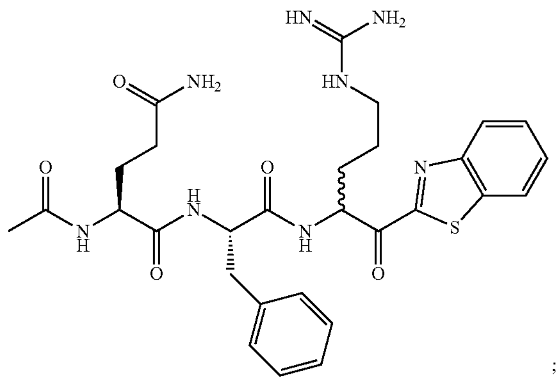
;
IIb
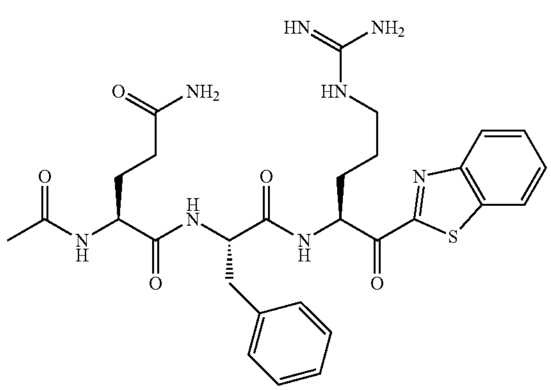
or
-continued
IIc
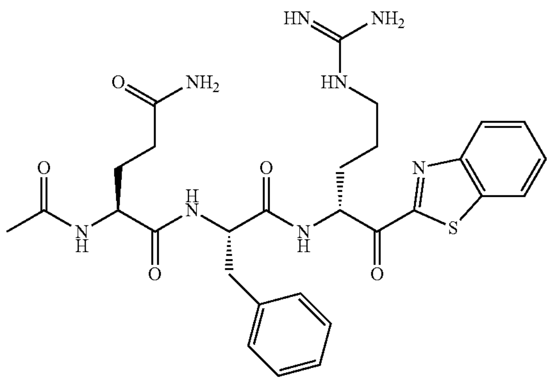
IIIa
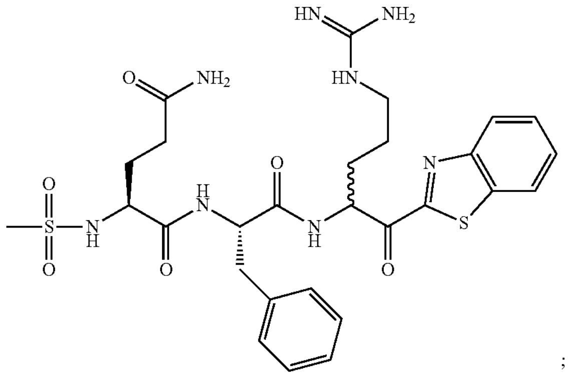
;
IIIb
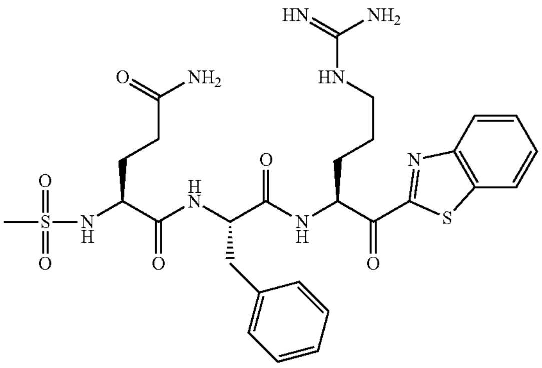
or
IIIc
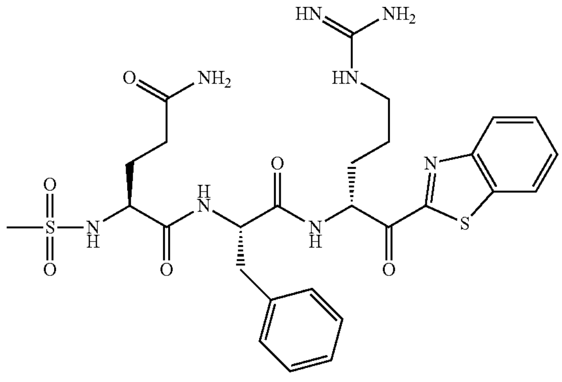
or a pharmaceutically acceptable salt thereof.

According to one aspect, there is provided a pharmaceutical composition comprising a compound as defined herein with a pharmaceutically acceptable carrier, diluent and excipient.

In one aspect, the present description relates to uses and methods of preventing and/or treating disorders associated with matriptase activity (in particular excess activity).

In one aspect, the present description relates to uses and methods of preventing and/or treating disorders described herein, in particular hyperproliferative disorders, tissue disorders, pain disorders, inflammatory disorders, respiratory disorders, viral infections or disorders associated with iron overload.

According to another aspect, there is provided the use of a compound or composition as defined herein in the manufacture of a medicament for the treatment or prevention of disorders associated with matriptase activity (in particular excess activity).

According to another aspect, there is provided the use of a compound or composition as defined herein in the manufacture of a medicament for the treatment or prevention of hyperproliferative disorders, tissue disorders, inflammatory disorders, respiratory disorders, viral infections or disorders associated with iron overload.

According to another aspect, there is provided a method for treating disorders associated with matriptase activity (in particular excess activity) in a subject in need thereof which comprises administering a therapeutically effective amount of a compound as defined herein.

According to another aspect, there is provided a method for treating hyperproliferative disorders, tissue disorders, inflammatory disorders, respiratory disorders, viral infections or disorders associated with iron overload in a subject in need thereof which comprises administering a therapeutically effective amount of a compound as defined herein Combinations of substituents and variables envisioned by the present description are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

In some embodiments, the present description also relates to one or more of the following embodiments:

Item 1. A compound of formula:

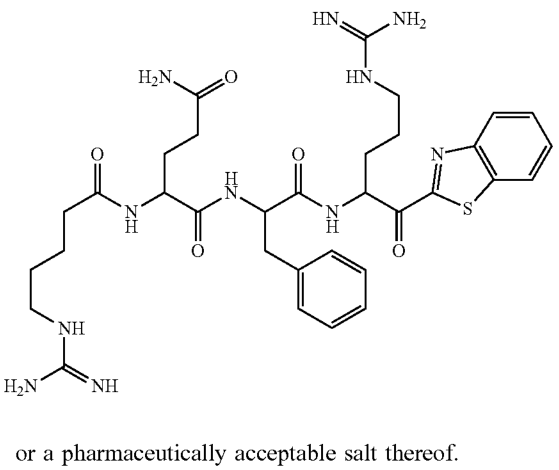

or a pharmaceutically acceptable salt thereof.

Item 2. A compound of formula:

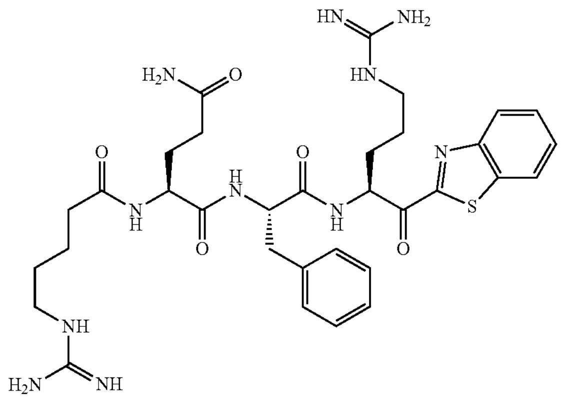

or a pharmaceutically acceptable salt thereof.

Item 3. A pharmaceutical composition comprising a compound according to item 1 or 2 and a pharmaceutically acceptable carrier, diluent and excipient.

Item 4. Compound according to item 1 or 2 or a pharmaceutical composition comprising said compound for preventing and/or treating disorders associated with matriptase activity.

Item 5. Use of a compound according to item 1 or 2 or a pharmaceutical composition comprising said compound for preventing and/or treating disorders associated with matriptase activity (in particular excess activity).

Item 6. Use of a compound according to item 1 or 2 in the manufacture of a medicament for the treatment or prevention of disorders associated with matriptase activity (in particular excess activity).

Item 7. Compound according to item 1 or 2 or a pharmaceutical composition comprising said compound for preventing and/or treating hyperproliferative disorders, tissue disorders, pain disorders, inflammatory disorders, respiratory disorders, viral infections or disorders associated with iron overload.

Item 8. Use of a compound according to item 1 or 2 or a pharmaceutical composition comprising said compound for preventing and/or treating hyperproliferative disorders, tissue disorders, inflammatory disorders, respiratory disorders, viral infections or disorders associated with iron overload.

Item 9. Use of a compound according to item 1 or 2 in the manufacture of a medicament for the treatment or prevention of hyperproliferative disorders, tissue disorders, inflammatory disorders, respiratory disorders, viral infections or disorders associated with iron overload.

Item 10. The use according to items 8 or 9, for the treatment or prevention of oral squamous cell carcinoma.

Item 11. The use according to items 8 or 9, for the treatment or prevention of osteoarthritis.

Item 12. The use according to items 8 or 9, for the treatment or prevention of idiopathic pulmonary fibrosis.

Item 13. The use according to items 8 or 9, for the treatment or prevention of influenza type A, B or C.

Item 14. A method for treating disorders associated with matriptase activity (in particular excess activity) in a subject in need thereof which comprises administering a therapeutically effective amount of a compound according to item 1 or 2 or a composition comprising said compound.

Item 15. A method for treating hyperproliferative disorders, tissue disorders, inflammatory disorders, respiratory disorders, viral infections or disorders associated with iron overload in a subject in need thereof which comprises administering a therapeutically effective amount of a compound according to item 1 or 2 or a composition comprising said compound.

Item 16. The method according to item 15, for the treatment or prevention of oral squamous cell carcinoma.

Item 17. The method according to item 15, for the treatment or prevention of osteoarthritis.

Item 18. The method according to item 15, for the treatment or prevention of idiopathic pulmonary fibrosis.

Item 19. The method according to item 15, for the treatment or prevention of influenza type A, B or C.

Item 20. The method according to anyone of items 14 to 19, wherein the subject is a human subject.

Item 21. A compound of formula:

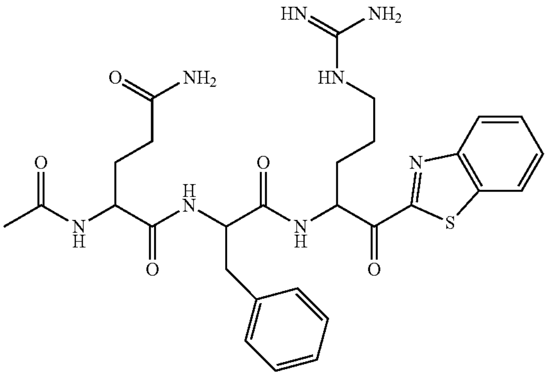 [SMILES: CC(=O)NC(CCC(N)=O)C(=O)NC(Cc1ccccc1)C(=O)NC(CCCNC(=N)N)C(=O)c1nc2ccccc2s1]

or a pharmaceutically acceptable salt thereof.

Item 22. A compound of formula:

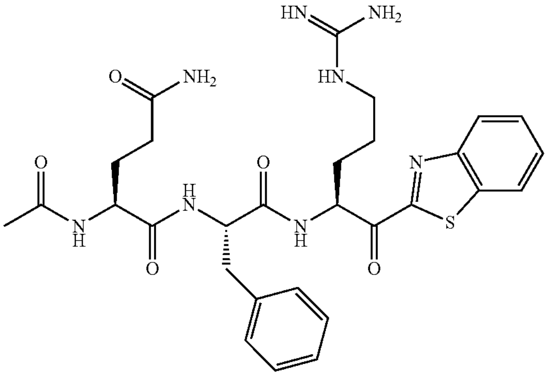 [SMILES: CC(=O)N[C@@H](CCC(N)=O)C(=O)N[C@@H](Cc1ccccc1)C(=O)N[C@@H](CCCNC(=N)N)C(=O)c1nc2ccccc2s1]

or a pharmaceutically acceptable salt thereof.

Item 23. A pharmaceutical composition comprising a compound according to Item 21 or 22 and a pharmaceutically acceptable carrier, diluent and excipient.

Item 24.: Compound according to Item 21 or 22 or a pharmaceutical composition comprising said compound for preventing and/or treating disorders associated with matriptase activity.

Item 25. Use of a compound according to Item 21 or 22 or a pharmaceutical composition comprising said compound for preventing and/or treating disorders associated with matriptase activity (in particular excess activity).

Item 26. Use of a compound according to Item 21 or 22 in the manufacture of a medicament for the treatment or prevention of disorders associated with matriptase activity (in particular excess activity).

Item 27. Compound according to Item 21 or 22 or a pharmaceutical composition comprising said compound for preventing and/or treating hyperproliferative disorders, tissue disorders, pain disorders, inflammatory disorders, respiratory disorders, viral infections or disorders associated with iron overload.

Item 28. Use of a compound according to Item 21 or 22 or a pharmaceutical composition comprising said compound for preventing and/or treating hyperproliferative disorders, tissue disorders, inflammatory disorders, respiratory disorders, viral infections or disorders associated with iron overload.

Item 29. Use of a compound according to Item 21 or 22 in the manufacture of a medicament for the treatment or prevention of hyperproliferative disorders, tissue disorders, inflammatory disorders, respiratory disorders, viral infections or disorders associated with iron overload.

Item 30. The use according to Item 28 or 29, for the treatment or prevention of oral squamous cell carcinoma.

Item 31. The use according to Item 28 or 29, for the treatment or prevention of osteoarthritis.

Item 32. The use according to Item 28 or 29, for the treatment or prevention of idiopathic pulmonary fibrosis.

Item 33. The use according to Item 28 or 29, for the treatment or prevention of influenza type A, B or C.

Item 34. A method for treating disorders associated with matriptase activity (in particular excess activity) in a subject in need thereof which comprises administering a therapeutically effective amount of a compound according to Item 21 or 22 or a composition comprising said compound.

Item 35. A method for treating hyperproliferative disorders, tissue disorders, inflammatory disorders, respiratory disorders, viral infections or disorders associated with iron overload in a subject in need thereof which comprises administering a therapeutically effective amount of a compound according to Item 21 or 22 or a composition comprising said compound.

Item 36. The method according to Item 35, for the treatment or prevention of oral squamous cell carcinoma.

Item 37. The method according to Item 35, for the treatment or prevention of osteoarthritis.

Item 38. The method according to Item 35, for the treatment or prevention of idiopathic pulmonary fibrosis.

Item 39. The method according to Item 35, for the treatment or prevention of influenza type A, B or C.

Item 40. The method according to any one of Items 35 to 39, wherein the subject is a human subject.

Item 41. A compound of formula:

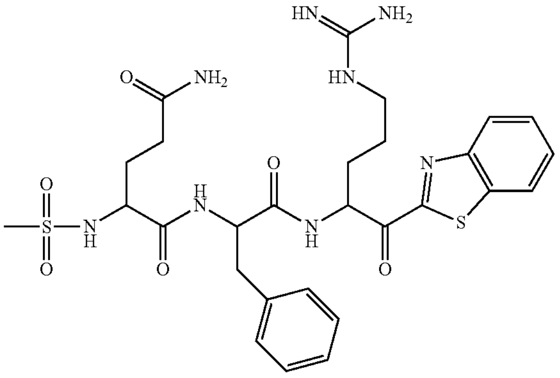 [SMILES: CS(=O)(=O)NC(CCC(N)=O)C(=O)NC(Cc1ccccc1)C(=O)NC(CCCNC(=N)N)C(=O)c1nc2ccccc2s1]

or a pharmaceutically acceptable salt thereof.

Item 42. A compound of formula:

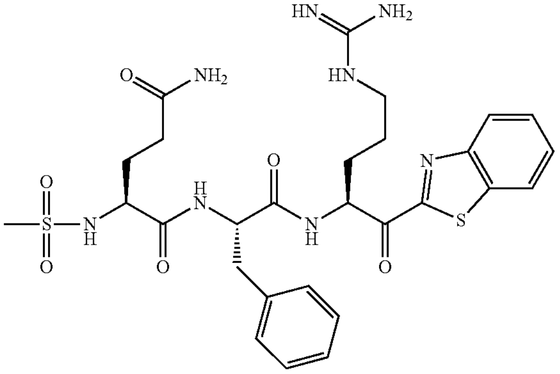 [SMILES: CS(=O)(=O)N[C@@H](CCC(N)=O)C(=O)N[C@@H](Cc1ccccc1)C(=O)N[C@@H](CCCNC(=N)N)C(=O)c1nc2ccccc2s1]

or a pharmaceutically acceptable salt thereof.

Item 43. A pharmaceutical composition comprising a compound according to Item 41 or 42 and a pharmaceutically acceptable carrier, diluent and excipient.

Item 44. Compound according to Item 41 or 42 or a pharmaceutical composition comprising said compound for preventing and/or treating disorders associated with matriptase activity.

Item 45. Use of a compound according to Item 41 or 42 or a pharmaceutical composition comprising said compound for preventing and/or treating disorders associated with matriptase activity (in particular excess activity).

Item 46. Use of a compound according to Item 41 or 42 in the manufacture of a medicament for the treatment or prevention of disorders associated with matriptase activity (in particular excess activity).

Item 47. Compound according to Item 41 or 42 or a pharmaceutical composition comprising said compound for preventing and/or treating hyperproliferative disorders, tissue disorders, pain disorders, inflammatory disorders, respiratory disorders, viral infections or disorders associated with iron overload.

Item 48. Use of a compound according to Item 41 or 42 or a pharmaceutical composition comprising said compound for preventing and/or treating hyperproliferative disorders, tissue disorders, inflammatory disorders, respiratory disorders, viral infections or disorders associated with iron overload.

Item 49. Use of a compound according to in Item 41 or 42 in the manufacture of a medicament for the treatment or prevention of hyperproliferative disorders, tissue disorders, inflammatory disorders, respiratory disorders, viral infections or disorders associated with iron overload.

Item 50. The use according to Item 48 or 49, for the treatment or prevention of oral squamous cell carcinoma.

Item 51. The use according to Item 48 or 49, for the treatment or prevention of osteoarthritis.

Item 52. The use according to Item 48 or 49, for the treatment or prevention of idiopathic pulmonary fibrosis.

Item 53. The use according to Item 48 or 49, for the treatment or prevention of influenza type A, B or C.

Item 54. A method for treating disorders associated with matriptase activity (in particular excess activity) in a subject in need thereof which comprises administering a therapeutically effective amount of a compound according to Item 41 or 42 or a composition comprising said compound.

Item 55. A method for treating hyperproliferative disorders, tissue disorders, inflammatory disorders, respiratory disorders, viral infections or disorders associated with iron overload in a subject in need thereof which comprises administering a therapeutically effective amount of a compound according to Item 41 or 42 or a composition comprising said compound.

Item 56. The method according to Item 55, for the treatment or prevention of oral squamous cell carcinoma.

Item 57. The method according to Item 55, for the treatment or prevention of osteoarthritis.

Item 58. The method according to Item 55, for the treatment or prevention of idiopathic pulmonary fibrosis.

Item 59. The method according to Item 55, for the treatment or prevention of influenza type A, B or C.

Item 60. The method according to any one of Items 55 to 59, wherein the subject is a human subject.

BRIEF DESCRIPTION OF THE DRAWINGS

FIG. 1. is a graph of the results from Example 6, showing that Compound 1 decreased the cartilage damage score in treated mice.

DETAILED DESCRIPTION

Methods, Uses, Formulation and Administration

Hyperproliferative Disorders

In one aspect, the compounds of the present description may be used to treat or prevent hyperproliferative disorders.

In one aspect, the compounds of the present description may be used for inhibiting tumor growth, progression and/or metastasis in a subject in need thereof.

In other specific embodiments, the hyperproliferative disorder is prostate adenocarcinoma, breast cancer, ovarian carcinoma, cervical neoplasia, small cell lung cancer, non-small cell lung cancer, colon cancer, liver cancer, pancreatic cancer, colon cancer, renal cell carcinoma, pancreatic ductal adenocarcinoma, uterine leiomyosarcoma, transitional cell carcinoma, nonmelanoma skin cancer, squamous cell carcinoma, melanoma, leukemia, larger cell carcinoma of the lymph node, central nervous system (CNS) cancer malignant mesothelioma or glioblastoma.

In one aspect the cancer is oral squamous cell carcinoma.

In one aspect, the subject is a cancer patient and is treated as long as the disease is stable or until there is tumor progression (e.g., diseases progression, appearance of new lesions etc.).

In one embodiment the compounds are used in combination with standard chemotherapy.

In one embodiment there is provided, a pharmaceutical composition comprising at least one compound as defined herein or a pharmaceutically acceptable salt thereof and one or more further therapeutic agent indicated for the treatment or prevention of cancer.

In one embodiment there is provided, a pharmaceutical composition comprising one compound as defined or a pharmaceutically acceptable salt thereof and one or more further therapeutic agent for inhibiting the proliferation of cancer cells or for the treatment or prevention of cancer.

Tissue Disorders

In additional embodiments, compounds of the present description can be used for the treatment or prevention of tissue or skin disorders, including in particular embodiments, atopic dermatitis, rosacea, psoriasis, ichthyosis, follicular atrophoderma, hyperkeratosis, hypotrichosis, Netherton syndrome and others.

In further particular embodiments, the pathological condition is characterized by epithelial cell proliferation or abnormal neovascularization.

Pain Disorders

Pain disorders include pain, acute pain, chronic pain, nociceptive pain, acute nociceptive pain, chronic nociceptive pain, neuropathic pain, acute neuropathic pain, chronic neuropathic pain, inflammatory pain, acute inflammatory pain, chronic inflammatory pain.

In a further embodiment, the compounds may be used for the treatment of pelvic pain, knee pain or peripheral neuropathy (primarily PHN).

Inflammatory Disorders

In one aspect, the compounds of the present description may also be used be used for the treatment or prevention of rheumatoid arthritis, chronic tendinitis, osteoarthritis, Crohn's disease, irritable bowel syndrome (IBS), ulcerative colitis or atherosclerosis.

In one aspect, the compounds of the present description may also be used be used for the treatment or prevention of osteoarthritis (e.g. knee).

Respiratory Disorders

In one aspect, the compounds of the present description may also be used be used for the treatment or prevention of idiopatic pulmonary fibrosis, cystic fibrosis, bronchitis, chronic obstructive pulmonary disease (COPD), asthma, allergic rhinitis, ciliary dyskinesia, lung carcinoma, pneumonia or a respiratory infection.

Idiopathic pulmonary fibrosis (IPF) is a progressing chronic fibrotic lung disease with a median survival of 2 to 3 years affecting people in the 50-79 year age group. The fibrosis is believed to result from epithelial injury, activation, and/or apoptosis with abnormal wound healing. It has been hypothesized that injuries of the lung lead to destruction of epithelial alveolar cells and that the resulting repair process is dysregulated, leading to the proliferation and migration of fibroblasts, transformation to myofibroblasts, and excessive collagen deposition within the lung interstitium and alveolar space. The pathogenesis of the disease is thought to be driven by the activation of multiple cell pathways including the endothelial growth factor (VEGF), the fibroblast growth factor (FGF) and the platelet-derived growth factor (PDGF). The serine protease matriptase is believed to play a driving role in the development of IPF, via activation of PAR-2 receptors (Bardou O, et al. Membrane-anchored Serine Protease Matriptase Is a Trigger of Pulmonary Fibrogenesis. Am J Respir Crit Care Med 2016; 193 (8)::847-60).

Viral Infections

In one aspect, the compounds of the present description may be used for the treatment or prevention of coronaviruses infections (e.g. a human infection).

In one aspect, the compounds of the present description may be used for the treatment or prevention of coronaviruses including human coronavirus HCoV-NL63, HCoV-OC43, HCoV-229E, HCoV-HKUI, SARS-CoV (Severe Acute Respiratory Syndrome-Corona Virus), and CoV MERS (Middle East Respiratory Syndrome virus, previously called "EMC").

In one aspect, the compounds of the present description may be used for the treatment or prevention of parainfluenza viruses infections "PIV" (e.g. a human infection).

In one aspect, the compounds of the present description may be used for the treatment or prevention of HPIV type 1, HPIV type 2, HPIV type 3 or HPIV type 4.

In one aspect, the compounds of the present description may be used for the treatment or prevention of orthomyxovirus infections.

In one aspect, the compounds of the present description may be used for the treatment or prevention of influenza type A, B or C infections.

In one aspect, the compounds of the present description may be used for the treatment or prevention of flu infections.

As used herein, the term "flu" and "flu infection" refers to an infectious disease caused by certain RNA viruses from the orthomyxoviridae (e.g., influenza virus) family. It includes infections by types A, B and C influenza viruses. It affects birds and mammals. The most common symptoms of the disease are chills, fever, sore throat, scratchy throat, muscle pains, headache, chest congestion, head congestion, coughing, weakness, exhaustion, loss of appetite and general discomfort.

Hemagglutinin (HA) protein plays an essential role in binding to and entering into host cells during the virus infection process. Hemagglutinin (HA) binds to monosaccharide sialic acids that are present on the surface of its target host cells. The cell membrane then engulfs the virus through endocytosis and forms endosomes. The binding affinity of a type of influenza virus to sialic acids on epithelial cells of the respiratory system, typically in the nose, pharynx, trachea, bronchi, bronchioles, alveoli and lungs of mammals and intestines of birds, can affect the capability of the virus to infect the species and the capability to spread among different individuals.

Influenza HA is synthesized as a single protein precursor termed HA0 and since the virus does not encode any protease, host cell proteases are required for the cleavage of HA0 into subunits HA1 and HA2. This cleavage is required for the protein to change conformation in the acidic conditions in the endosome. This change in the protein's conformation exposes the hydrophobic fusion peptide located in the HA2 subunit. This allows the virus to fuse with the host cell. The hemagglutinin proteins of pathogenic avian influenza viruses are characterized by multibasic cleavage sites containing furin-like recognition sequences RXXR. Since some subtilisin-like proteases such as furin or other proprotein convertases are ubiquitous, the HA glycoprotein of avian viruses utilizes multiple tissues and sites for its activation and allows infection and replication of these viruses in many cell types (pantropicity). One of the severe manifestations of avian flu virus is a life-threatening encephalitis. On the other hand, the HA glycoprotein of non-avian viruses does not have the polybasic furin-recognition site. These viruses have monobasic cleavage sites recognized by other proteases (e.g., TTSPs) of the host.

In one embodiment there is provided, a pharmaceutical composition comprising at least one compound as defined herein or a pharmaceutically acceptable salt thereof and one or more further therapeutic agent indicated for the treatment or prevention of orthomyxovirus infections (e.g. influenza).

In one said further therapeutic agent is a viral M2 ion channel inhibitor or a neuraminidase inhibitor. In another specific embodiment, said further therapeutic agent is Tamiflu™ (oseltamivir), Relenza™ (zanamivir), laninamivir, peramivir, amantadine, rimantadine, ribavirin, vitamin C, Cold Fx™, echinacea, ginseng or any combination thereof.

Disorders Associated with Iron Overload

In one aspect, the compounds of the present description may be used for the treatment or prevention disorders associated with iron overload. Iron overload is a condition characterized by increased levels of iron. Iron overload can result in excess iron deposition in various tissues and can lead to tissue and organ damage.

In one aspect, the iron overload disorder is thalassemia (e.g. β-thalassemia) or hemochromatosis.

Formulations

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

In some embodiments, the therapeutically effective amount of a compound as defined herein, or a pharmaceutically acceptable salt thereof, can be administered to a subject alone or admixed with a pharmaceutically acceptable carrier.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of the present description that, upon administration to a recipient, is capable of providing, either directly or indirectly, a compound of the present description or an inhibitory active metabolite or residue thereof.

Compositions described herein may be administered orally, parenterally, by inhalation spray, dry powder inhalation, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of the present description with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the present description include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present description. Additionally, the description contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

In another specific embodiment, the composition comprising at least one compound as defined herein or a pharmaceutically acceptable salt thereof is formulated for direct administration into lungs. In another specific embodiment the composition is formulated for administration by an inhaler or nebulizer.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the subject to be treated and the particular mode of administration. Provided compositions may be formulate such that a dosage of between 0.01-100 mg/kg body weight/day of the inhibitor can be administered to a subject receiving these compositions.

It should also be understood that a specific dosage and treatment regimen for any particular subject will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Compounds or compositions described herein may be administered using any amount and any route of administration effective for treating or lessening the severity of the disorders or diseases as contemplated herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the subject to be treated. It will be understood, however, that the total daily usage of the compounds and compositions of the present disclosure will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Combinations

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the composition of a compound or compounds described herein can be in combination with an additional therapeutic agent.

It will be understood, however, that the total daily usage of the compounds and compositions of the present description will be decided by the attending physician within the scope of sound medical judgment. The specific inhibitory dose for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The total daily dose of the compounds of the present description administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present description comprise administration to a subject in need of such treatment from about 10 mg to about 1000 mg of the compound(s) of the present description per day in single or multiple doses.

As used herein, the term "combination," "combined," and related terms refers to the simultaneous or sequential administration of therapeutic agents in accordance with the present description. For example, a provided compound may be administered with another therapeutic agent simultaneously or sequentially in separate unit dosage forms or together in a single unit dosage form. Accordingly, an embodiment of the present description provides a single unit dosage form comprising a provided compound, an additional therapeutic agent, and a pharmaceutically acceptable carrier, adjuvant, or vehicle for use in the methods of the present description.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 g/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, subjects using stents or other implantable devices risk clot formation or platelet activation. These unwanted effects may be prevented or mitigated by pre-coating the device with a pharmaceutically acceptable composition comprising a provided compound. Implantable devices coated with a compound of the present description are another embodiment of the present description.

In another aspect, the present description provides a method of method of synthesizing a compound of any of the formulae herein. Another embodiment is a method of making a compound of any of the formulae herein using any one, or combination of, reactions delineated herein. The method can include the use of one or more intermediates or chemical reagents delineated herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Definitions

As used herein, the singular forms "a", "an" and "the" are intended to include the plural forms as well, unless the context clearly indicates otherwise. To the extent that the terms "including", "includes", "having", "has", "with", or variants thereof are used in either the description and/or the claims, such terms are intended to be inclusive in a manner similar to the term "comprising."

The term "about" or "approximately" means within an acceptable error range for the particular value as determined by a person skilled in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Definitions of specific functional groups and chemical terms are described in more detail below. For purposes of the present description, the chemical elements are identified in accordance with the Periodic Table of the Elements, CAS version, Handbook of Chemistry and Physics, $75^{th}$, Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$, Edition, John Wiley & Sons, Inc., New York, 2001; Larock, Comprehensive Organic Transformations, VCH Publishers, Inc., New York, 1989; Carruthers, Some Modern Methods of Organic Synthesis, $3^{rd}$ Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present description. Unless otherwise stated, all tautomeric forms of the compounds are within the scope of the present description. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of the present description. Such compounds are useful, for example, as analytical tools, as probes in biological assays, or as therapeutic agents in accordance with the present description.

Where a particular enantiomer or diastereoisomer is preferred, it may, in some embodiments be provided substantially free of the corresponding enantiomer or corresponding diastereoisomer(s), and may also be referred to as "optically enriched" or "diastereoisomerically enriched". "Optically-enriched" or "diastereoisomerically enriched" as used herein, means that the compound is made up of a significantly greater proportion of one enantiomer or diastereoisomer. In certain embodiments, the compound is made up of at least about 90% by weight of a preferred enantiomer or diastereoisomer. In other embodiments, the compound is made up of at least about 95%, 98%, or 99% by weight of a preferred enantiomer or diastereoisomer. Preferred enantiomers or diastereoisomers may be isolated by any method known to those skilled in the art, including chiral high pressure liquid chromatography (HPLC) and the formation and crystallization of chiral salts or prepared by asymmetric syntheses. See, for example, Jacques et al., Enantiomers, Racemates and Resolutions (Wiley Interscience, New York, 1981); Wilen, et al., *Tetrahedron* 33:2725 (1977); Eliel, E. L. Stereochemistry of Carbon Compounds (McGraw-Hill, N Y, 1962); Wilen, S. H. Tables of Resolving Agents and Optical Resolutions, p. 268 (E. L. Eliel, Ed., Univ. of Notre Dame Press, Notre Dame, Ind. 1972).

The synthesized compounds may be separated from a reaction mixture and further purified by a method such as column chromatography, high pressure liquid chromatography, or recrystallization. Synthetic chemistry transformations and protecting group methodologies (protection and deprotection) useful in synthesizing the compounds described herein include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Compounds of the present description (e.g. formula (I), (II) and (Ill) include pharmaceutically acceptable salts, esters and prodrugs thereof.

The term "pharmaceutically acceptable salt" refers to those salts of the compounds formed by the process of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the present description, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present description which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the description. "Prodrug", as used herein means a compound which is convertible in vivo by metabolic or chemical means (e.g. by hydrolysis) to afford any compound delineated by the formulae of the instant description. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., *Journal of Drug Deliver Reviews,* 8:1-38(1992); Bundgaard, *J. of Pharmaceutical Sciences,* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology", John Wiley and Sons, Ltd. (2002).

EXAMPLES

As used herein, the following abbreviations may have the following meanings:

| Abbreviation | Term |
|---|---|
| ACN | Acetonitrile |
| DCM | Dichloromethane |
| DIPEA | N,N-Diisopropylethylamine |
| DMF | N,N-dimethyl formamide |
| DPM | Dess-Martin periodinane |
| EtOAc | Ethyl acetate |
| HATU | (dimethylamino)-N,N-dimethyl(3H-[1,2,3]triazolo[4,5-b]pyridin-3-yloxy)methaniminium hexafluorophosphate |
| HCl | Hydrochloric acid |
| HFIP | Hexafluoroisopropanol |
| iPrOH | Isopropanol |
| UPLC-Ms | Ultra perfomance liquid chromatography mass spectrum |
| min | Minute(s) |
| MeOH | Methanol |
| MsCl | Methanesulfonyl chloride |
| Mtr | 4-Methoxy-2,3,6-trimethylbenzenesulphonyl |
| NMR | Nuclear magnetic resonance |
| SFC | Supercritical fluid chromatography |
| THF | Tetrahydrofuran |
| TFA | Trifluoroacetic acid |

Example 1: Synthesis of Compound 1

Scheme 1. Solid phase synthesis of (H)Arg(Boc)2-Gln(Trt)-Phe (7).

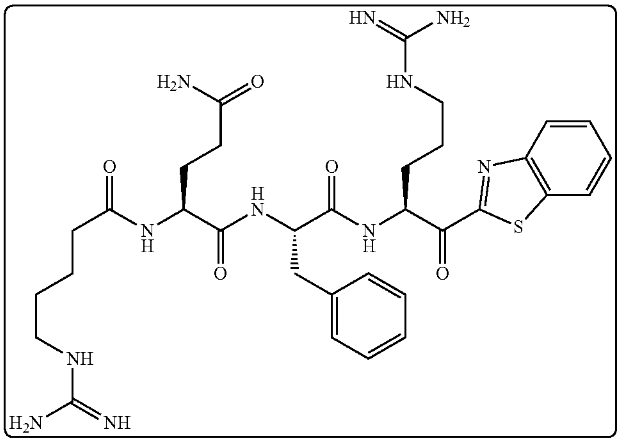

-continued

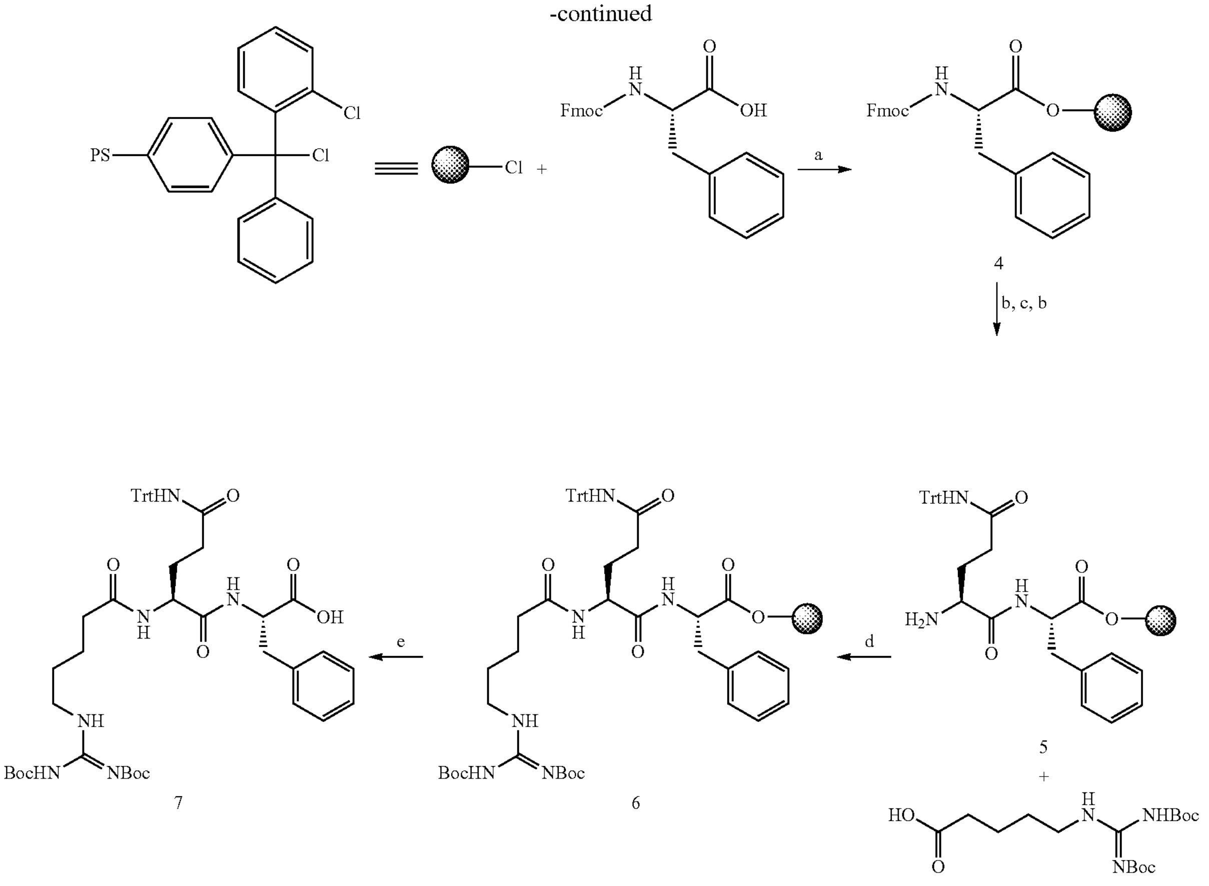

4

5

6

7

8

Reagents and conditions:
(a) DCM, DIPEA
(b) Piperidine/DMF (20:80)
(c) Fmoc-Gln(Trt)-OH, HATU, DIPEA, DMF
(d) 8, HATU, DIPEAM DMF
(e) HFIP/DCM (20:80)

Fmoc-Phe-Resin, Intermediate 4:

To 10 g of CTC Resin with a loading of 1.2 mmol/g were added Fmoc-Phe-OH (9.3 g, 24 mmol, 2 eq) dissolved in DCM (approximately 10 mL per gram of resin), and DIPEA (6.3 mL, 3 eq). The mixture was shaken vigorously for 30-60 min. To endcap any remaining reactive trityl chloride groups, HPLC grade methanol was added (0.8 mL per gram of resin), and mixed for 15 minutes. The resin was filtered and washed with 3xDCM, 2xDMF, 2xDCM, 3xiPrOH, 3xDCM, then dried in vacuo.

$NH_2$-Gln(Trt)Phe-Resin, Intermediate 5:

A solution of DMF/piperidine (20%) was added to the resin, which was then gently shaken for 30 minutes. The resin was filtered and washed with 3xDMF, iPrOH, 3xDCM then dried in vacuo. A solution of Fmoc-Gln(Trt)-OH (14.6 g, 24 mmol, 2 eq), HATU (9.3 g, 24 mmol, 2 eq) and DIPEA (1.05 mL, 6 mmol, 5 eq) were dissolved in DMF (approximately 10 mL per gram of resin), was added on resin. The resin was shaken for 2 h, filtered, then with 3xDMF, iPrOH, 3x DCM then dried in vacuo. A solution of DMF/piperidine (20%) was added to the resin, which was then gently shaken for 30 minutes. The resin was filtered and washed with 3xDMF, iPrOH, 3xDCM then dried in vacuo.

(H)Arg$(Boc)_2$-Gln(Trt)-Phe-Resin, Intermediate 6:

A solution of (H)Arg$(Boc)_2$-OH 8 (8.7 g, 24 mmol, 3 eq), HATU (9.3 g, 24 mmol, 3 eq) and DIPEA (1.05 mL, 6 mmol, 5 eq) were dissolved in DMF (approximately 10 mL per gram of resin), and was added on to the resin. The resin was shaken for 2 h, filtered, washed with 3xDMF, iPrOH, 3xDCM then dried in vacuo.

(H)Arg$(Boc)_2$-Gln(Trt)-Phe-OH Intermediate 7:

To 10 g of derivatized resin was added a solution 20% HFIP in DCM and shaken for 45 minutes. After removal of the solution, the resin was washed with DCM/HFIP (20%), 3xDCM. After suspension and co-evaporation in diethylether, the white solid was filtrated and dried in vacuo to give tripeptide 7 as a white solid (8.8 g). The compound was used as it in the next step without purification. Purity: >95% by UPLC.

Scheme 2. Solution synthesis of compound 1.

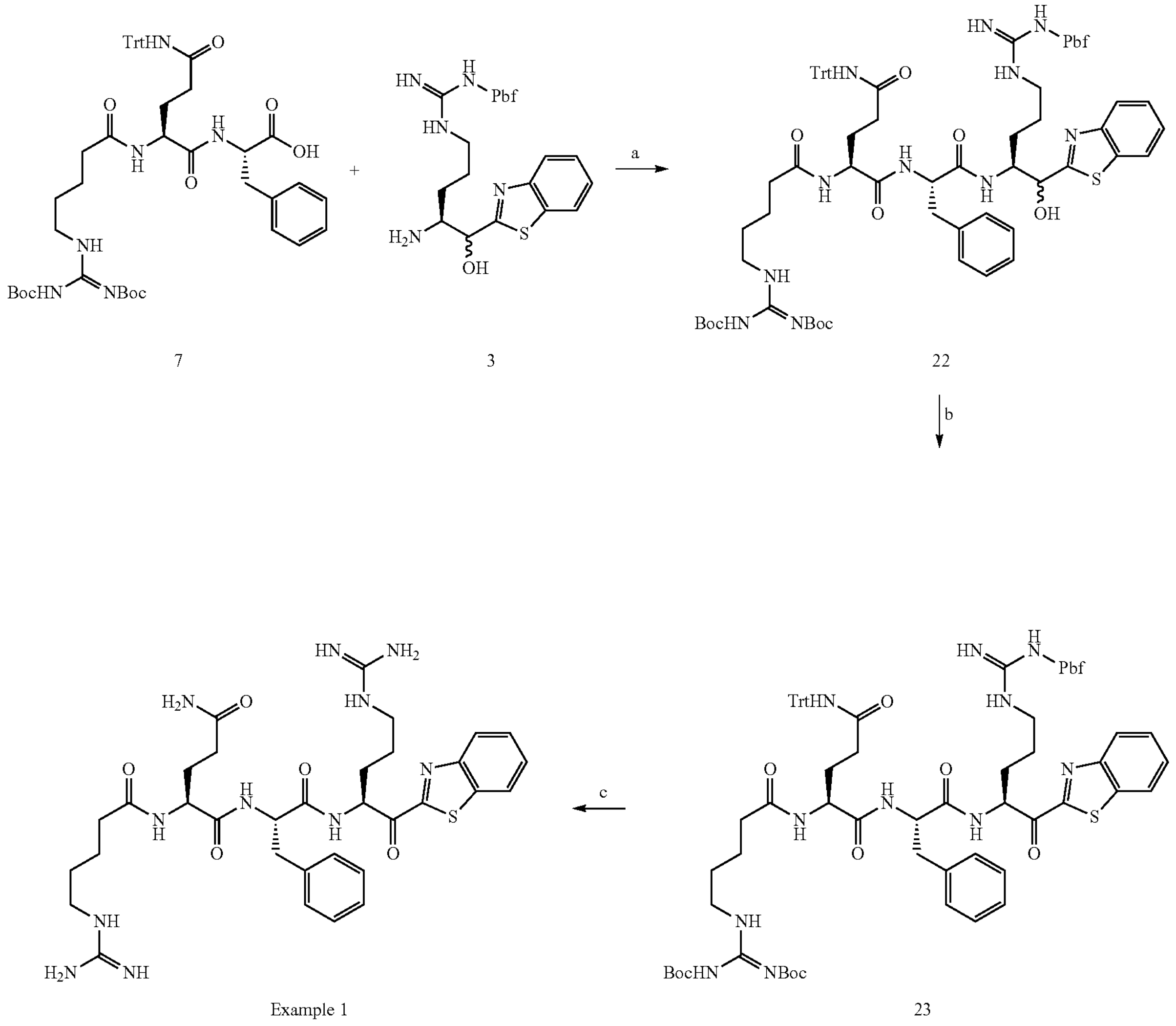

7 3 22

Example 1 23

Reagents and conditions: (a) HATU, DIPEA, DMF, 74% (b) DMP, DCM, 86%. (c) TFA/$H_2O$ (95:5)

Scheme 2. Solution Synthesis of Compound 1. Reagents and Conditions:

(a) HATU, DIPEA, DMF, 74% (b) DMP, DCM, 86%. (c) TFA/$H_2O$ (95:5)

To a solution of Intermediate 7 (3.72 g, 4.25 mmol, 1 eq) in anhydrous DMF were added HATU (1.61 g, 4.25 mmol, 1.1 eq), amine 3 (2.55 g, 4.68 mmol, 1.1 eq), and DIPEA (2.2 mL, 12.7 mmol, 3 eq) at 0° C. The mixture was stirred 15 minutes. The tetrapeptide was precipitated in cold water (0° C.), filtrated and washed twice with cold water. The filtrate was dissolved in ethyl acetate, washed with aqueous citric acid (10%) and brine. The organic phase was dried with sodium sulfate, filtrated and evaporated. The white solid was triturated in ether and purified by flash chromatography (MeOH/DCM 1:99 to MeOH/DCM 5:95). Intermediate 22 was obtained as a white solid (3.2 g, 52%).

DMP (1.2 g, 2.8 mmol, 1.4 eq) was added to a solution of protected tetrapeptide 22 (2.8 g, 2 mmol, 1 eq) in DCM for 15 minutes. The solution was washed with water, aqueous citric acid 10% and brine. The organic phase was dried with sodium sulfate and evaporated. The residue was triturated in cold ether and purified by flash chromatography (MeOH/DCM 1:99 to MeOH/DCM 5:95) to give the desired intermediate 23 as a white solid (2.4 g, 86%).

2.4 g of intermediate 23 is dissolved in a mixture of 20 mL of TFA/$H_2O$ (95:5) and stirred for 1 hour, until completion of the reaction by UPLC-MS. The TFA/$H_2O$ solution was added dropwise to 2×35 ml of cold water (0° C.) in two centrifugation tubes and then centrifuged at 4000 rpm for 30 minutes. The supernatant was removed and the white precipitated dissolved in water, washed with ether and lyophilized. A >95:5 mixture of diastereomer in favor of the S diastereomer of the arginine alpha carbon was obtained (1.3 g).

Compound is purified by reverse phase prep-HPLC MS (C18) using a ACN/water gradient (0.1% TFA) from 10 to 30% of ACN. As an example, 27 mg of pure compound was obtained from 50 mg of crude.

UPLC-Ms Retention time: 1.19 min

Purity: >99%

HRMS: Calculated for $C_{33}H_{45}N_{11}O_5S$: 708.3404 ($MH^+$); Found: 708.3534 ($MH^+$)

Example 2: Synthesis of Compound 2
Scheme 3. Solid phase synthesis of Ac-Gln(Trt)-Phe-OH (7).
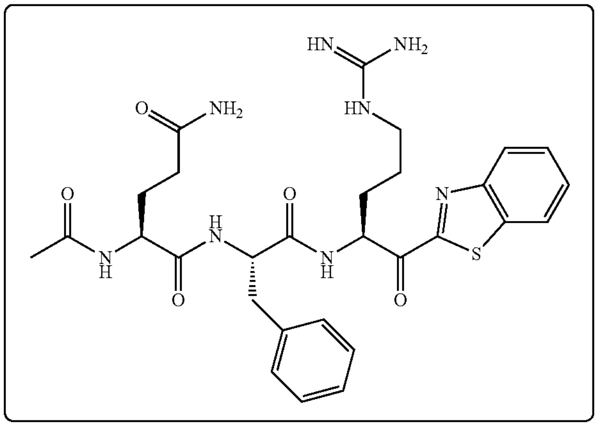
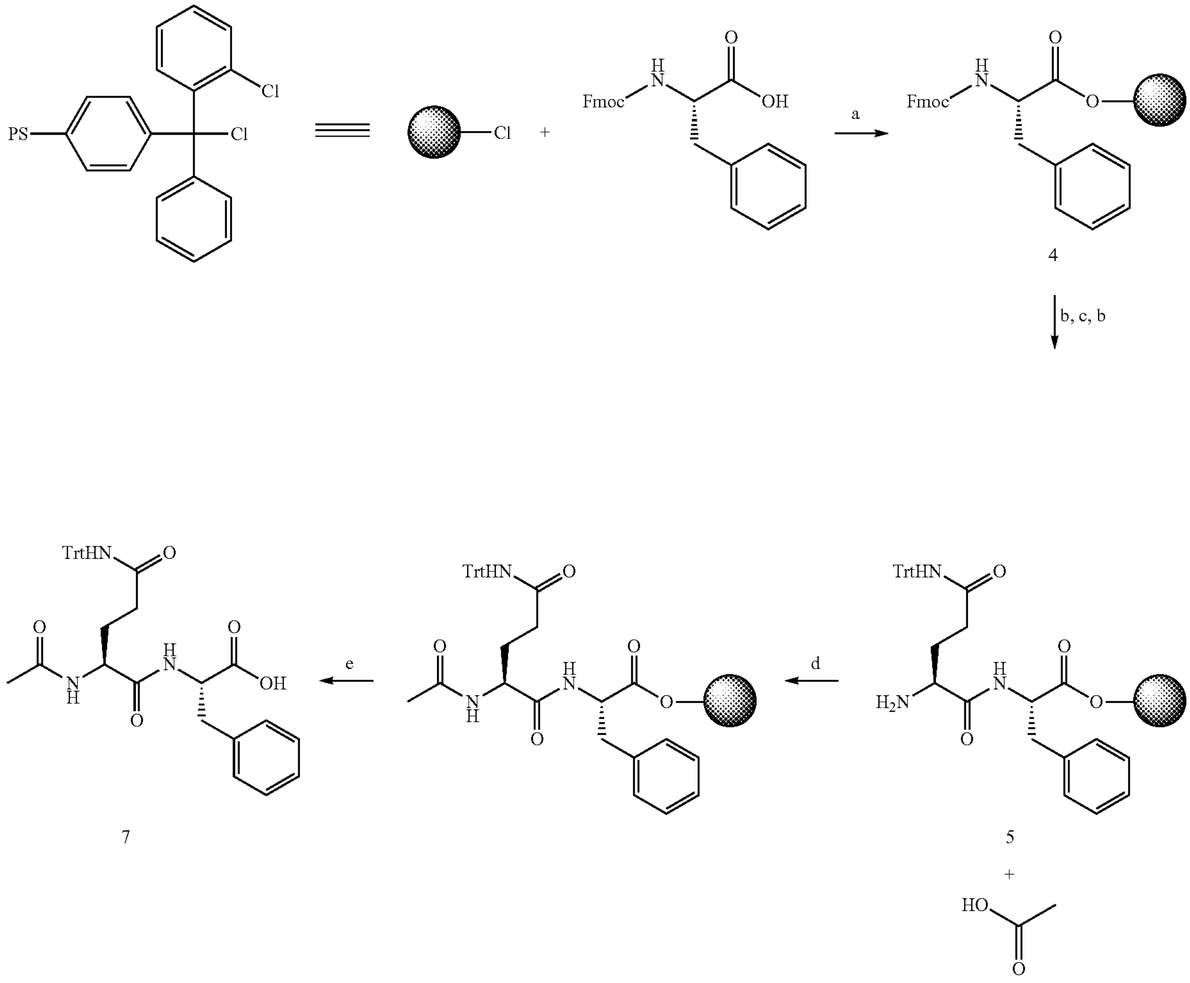
4
5
+
8
7
Reagents and conditions: (a) DCM, DIPEA (b) Piperidine/DMF (20:80) (c) Fmoc-Gln(Trt)-OH, HATU, DIPEA, DMF (d) 8, HATU, DIPEA, DMF (e) HFIP/DCM (20:80)

Fmoc-Phe-Resin, Intermediate 4:

To 10 g of CTC Resin with a loading of 1.2 mmol/g were added Fmoc-Phe-OH (9.3 g, 24 mmol, 2 eq) dissolved in DCM (approximately 10 mL per gram of resin), and DIPEA (6.3 mL, 3 eq). The mixture was shaken vigorously for 30-60 min. To endcap any remaining reactive trityl chloride groups, HPLC grade methanol was added (0.8 mL per gram of resin), and mixed for 15 minutes. The resin was filtered and washed with 3xDCM, 2xDMF, 2xDCM, 3xiPrOH, 3xDCM, then dried in vacuo. $NH_2$-Gln(Trt)Phe-Resin, Intermediate 5:

per gram of resin), and was added onto the resin. The resin was shaken for 2 h, filtered, washed with 3xDMF, iPrOH, 3xDCM then dried in vacuo.

Ac-Gln(Trt)-Phe-OH Intermediate 7:

To 10 g of derivatized resin was added a solution 20% HFIP in DCM and shaken for 45 minutes. After removal of the solution, the resin was washed with DCM/HFIP (20%), 3xDCM. After suspension and co-evaporation in diethylether, the white solid was filtrated and dried in vacuo to give tripeptide 7 as a white solid (6.7 g). The compound was used as it in the next step without purification. Purity: >95%.

Scheme 4. Solution synthesis of Compound 1.

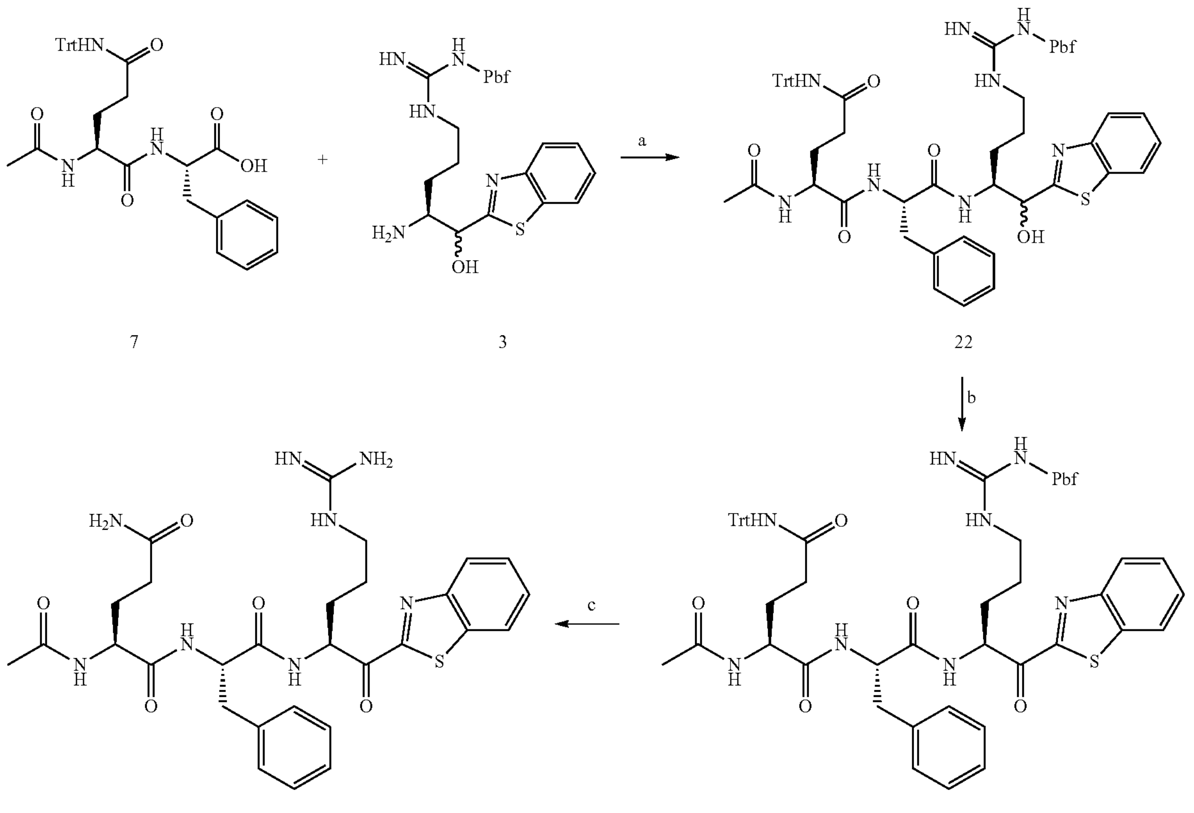

7 3 22

23

Example 2

Reagents and conditions: (a) HATU, DIPEA, DMF, 74% (b) DMP, DCM, 48%. (c) TFA/$H_2O$ (95:5)

A solution of DMF/piperidine (20%) was added to the resin, which was then gently shaken for 30 minutes. The resin was filtered and washed with 3xDMF, iPrOH, 3xDCM then dried in vacuo. A solution of Fmoc-Gln(Trt)-OH (14.6 g, 24 mmol, 2 eq), HATU (9.3 g, 24 mmol, 2 eq) and DIPEA (1.05 mL, 6 mmol, 5 eq) were dissolved in DMF (approximately 10 mL per gram of resin), and added onto the resin. The resin was shaken for 2 h, filtered, then with 3xDMF, iPrOH, 3xDCM then dried in vacuo. A solution of DMF/piperidine (20%) was added to the resin, which was then gently shaken for 30 minutes. The resin was filtered and washed with 3xDMF, iPrOH, 3xDCM then dried in vacuo.

Ac-Gln(Trt)-Phe-Resin, Intermediate 6:

A solution of acetic acid (1.8 mL, 30 mmol, 2.5 eq), HATU (12 g, 30 mmol, 2.5 eq) and DIPEA (10 mL, 60 mmol, 5 eq) were dissolved in DMF (approximately 10 mL To a solution of Intermediate 7 (3.5 g, 6.1 mmol, 1 eq) in anhydrous DMF (45 mL) was added HATU (2.6 g, 6.9 mmol, 1.1 eq), amine 3 (3.7 g, 6.9 mmol, 1.1 eq), and DIPEA (3.25 mL, 10.2 mmol, 3 eq) at 0° C. The mixture was stirred 15 minutes. The solution was poured in cold water (0° C.), filtrated and washed twice with cold water. The filtrate was dissolved in ether and DCM, washed with aqueous citric acid (10%) and brine. The organic phase was dried with sodium sulfate, filtrated and evaporated. The white solid was triturated in ether/hexane. The white solid was filtrated and used as it without purification. (5.3 g)

DMP (3 g, 7 mmol, 1.5 eq) was added to a solution of tetrapeptide 22 (5.2 g, 4.7 mmol, 1 eq) in DCM for 15 minutes. The solution was washed with water, aqueous citric acid 10% and brine. The organic phase was dried with sodium sulfate and evaporated. The residue was triturated in cold ether and purified by flash chromatography (EtOAc/

Hexane 10:90 0:100) to give the desired intermediate 23 as a white solid (3.5 g) 3 g of intermediate 23 is dissolved in a mixture of 20 mL of TFA/$H_2O$ (95:5) and stirred for 1 hours, until completion of the reaction by UPLC-MS. The TFA/$H_2O$ solution is added dropwise to 2×35 ml of cold water (0° C.) in two centrifugation tubes and then centrifuged at 4000 rpm for 30 minutes. The supernatant is removed and the white precipitated is dissolved in water and washed with ether. A≈90:10 mixture of diastereomer in favor of the S diastereomer of the arginine alpha carbon is obtained (2.0 g)

Compound is purified by reverse phase prep-HPLC MS (C18) using a ACN/water gradient (0.1% TFA) from 20 to 40% of ACN. For example, 38 mg of pure compound was obtained from 50 mg of crude.

UPLC-Ms Retention time: 1.28 min

Purity: 99%

HRMS: Calculated for $C29H_{36}N_8O_5S$: 609.2602 ($MH^+$); Found: 609.2621 ($MH^+$)

Example 3: Synthesis of Compound 3

Scheme 5: Mesylation of Gnl(Trt)

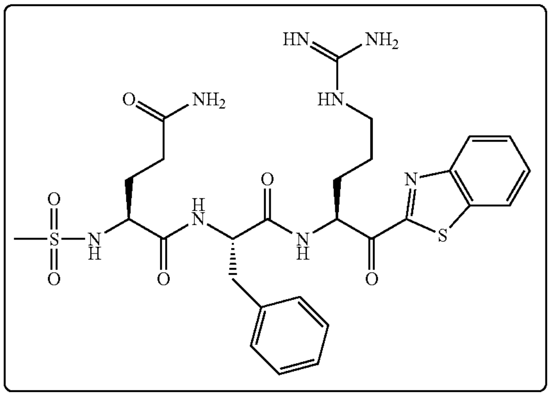

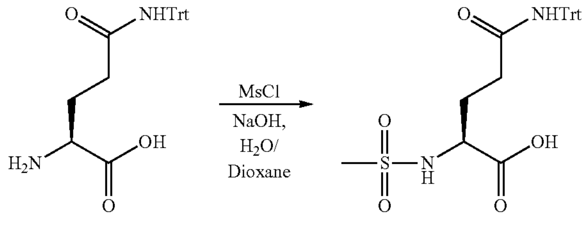

Gln(Trt)-OH (10 g, 25.7 mmol, 1 eq.) was dissolved in 1.5N NaOH (25 mL) and dioxane (75 mL) was added and cooled at 0° C. MsCl (2.7 ml, 25.7 mmol, and NaOH 1.5N was added dropwise to maintain the pH to 9-10 for 2 h and at room temp. for 2 h. Dioxane is evaporated and ether is added. The precipitate is filtrated and the solid dissolved in DCM/Ether and dried with sodium sulfate. A white solid is obtained (7.2 g) and used in next step without purification.

Scheme 6. Solid phase synthesis of Ms-Gln(Trt)-Phe-OH (7).

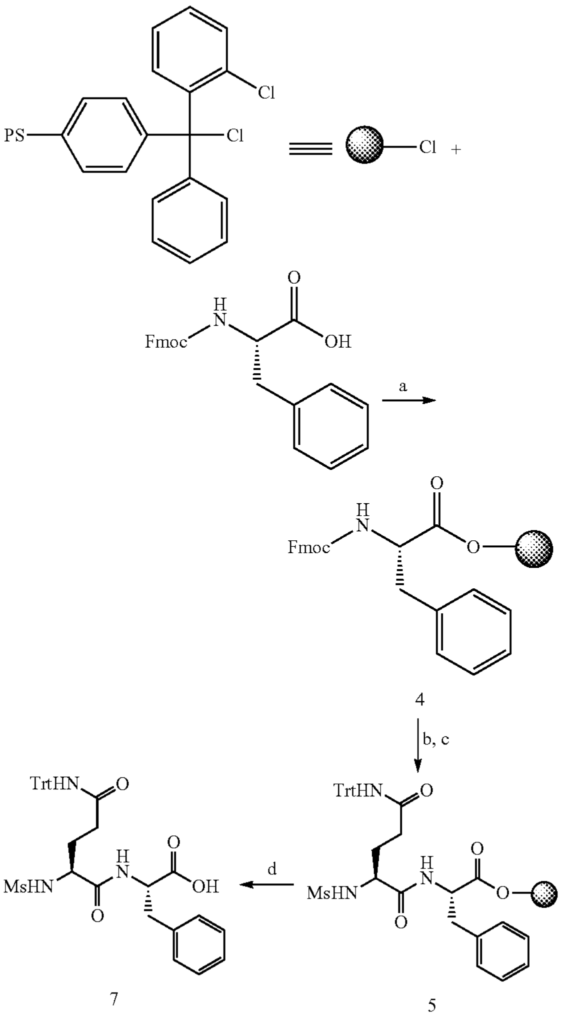

4

7

5

Reagents and conditions:
(a) DCM, DIPEA
(b) Piperidine/DMF (20:80)
(c) Ms-Gln(Trt)-OH, HATU, DMF
(d) HFIP/DCM (20:80)

Fmoc-Phe-Resin, Intermediate 4:

To 4 g of CTC Resin with a loading of 1.2 mmol/g was added Fmoc-Phe-OH (4.6 g, 12 mmol, 2 eq) dissolved in DCM (approximately 10 mL per gram of resin), and DIPEA (3.2 mL, 3 eq). The mixture was shaken vigorously for 30-60 min. To endcap any remaining reactive trityl chloride groups, HPLC grade methanol was added (0.8 mL per gram of resin), and mixed for 15 minutes. The resin was filtered and washed with 3×DCM, 2×DMF, 2×DCM, 3×iPrOH, 3×DCM, then dried in vacuo.

Ms-Gln(Trt)Phe-Resin, Intermediate 5: A solution of DMF/piperidine (20%) was added to the resin, which was then gently shaken for 30 minutes. The resin was filtered and washed with 3×DMF, iPrOH, 3×DCM then dried in vacuo. A solution of Ms-Gln(Trt)-OH (5.35, 12 mmol, 3 eq), HATU (4.6 g, 12 mmol, 3 eq) and DIPEA (3.5 mL, 20 mmol, 5 eq) were dissolved in DMF (approximately 10 mL per gram of resin), and was added onto the resin. The resin was shaken for 2 h, filtered, then with 3×DMF, iPrOH, 3×DCM then dried in vacuo.

Ms-Gln(Trt)-Phe-OH Intermediate 7:

To 4 g of derivatized resin was added a solution 20% HFIP in DCM and shaken for 45 minutes. After removal of the solution, the resin was washed with DCM/HFIP (20%), 3xDCM. After suspension and co-evaporation in diethylether, a white solid was obtained after flash chromatography purification (1.9 g). Purity: >95%.

cold ether and purified by flash chromatography (EtOAc/Hexane 10:90 0:100) to give the Intermediate 23 as a white solid (1.6 g) 1.6 g of intermediate 23 was dissolved in a mixture of 20 mL of TFA/$H_2O$ (95:5) and stirred for 1 hour, until completion of the reaction by UPLC-MS. The TFA/$H_2O$ solution is added dropwise to 2x35 ml of cold water (0° C.) in two centrifugation tubes and then centrifuged at 4000

Scheme 7. Solution synthesis of Example 3.

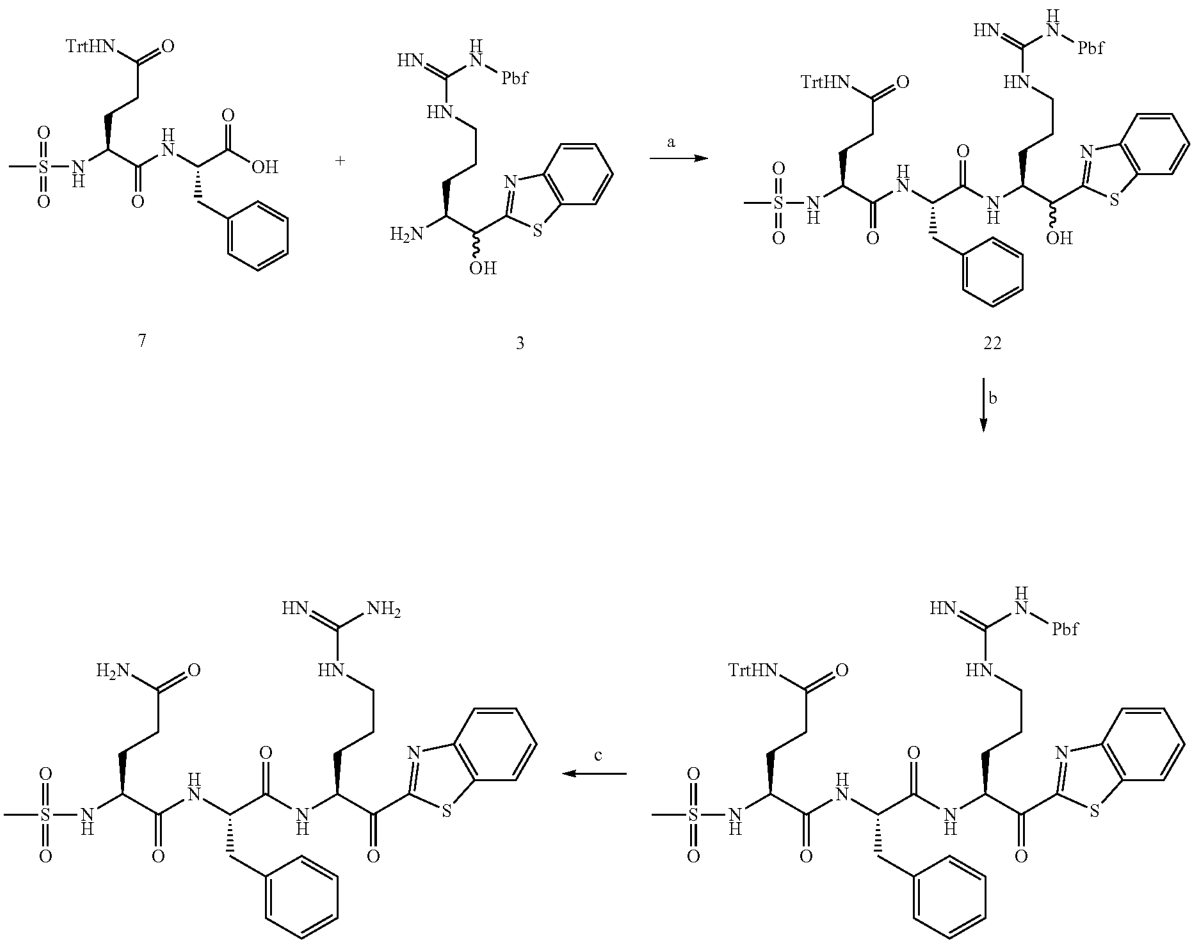

7 3 22

Example 3 23

Reagents and conditions: (a) HATU, DIPEA, DMF, 74% (b) DMP, DCM, 86%. (c) TFA/$H_2O$ (95:5)

To a solution of Intermediate 7 (1.8 g, 2.9 mmol, 1 eq) in anhydrous DMF was added HATU (1.1 g, 2.9 mmol, 1 eq), amine 3 (1.74 g, 3.2 mmol, 1.1 eq), and DIPEA (1.5 mL, 8.7 mmol, 3 eq) at 0° C. The mixture was stirred 15 minutes. The solution was poured into cold water (0° C.), filtrated, and washed with cold water twice. The filtrate was dissolved in ethyl acetate, washed with aqueous citric acid (10%) and brine. The organic phase was dried with sodium sulfate, filtrated and evaporated. The white solid was triturated in ether and filtrated to give intermediate 22 as a white solid (3.1 g).

DMP (1.6 g, 5.25 mmol, 1.5 eq) was added to a solution of tetrapeptide 22 (2.9 g, 3.5 mmol, 1 eq) in DCM for 15 minutes. The solution was washed with water, aqueous citric acid 10% and brine. The organic phase was dried with sodium sulfate and evaporated. The residue was triturated in rpm for 30 minutes. The supernatant is removed and the white precipitated is dissolved in water, washed with ether and lyophilized. A >95:5 mixture of diastereomer in favor of the S diastereomer of the arginine alpha carbon is obtained (0.8 g).

The compound was purified by reverse phase prep-HPLC MS (C18) using a ACN/water gradient (0.1% TFA) from 20 to 40% of ACN. For example, 32 mg of pure compound was obtained from 50 mg of crude.

UPLC-Ms Retention time: 1.27 min

Purity: 99%

HRMS: Calculated for $C_{28}H_{36}N_8O_6S_2$: 645.2272 ($MH^+$); Found: 645.2305 ($MH^+$)

Building Block Synthesis

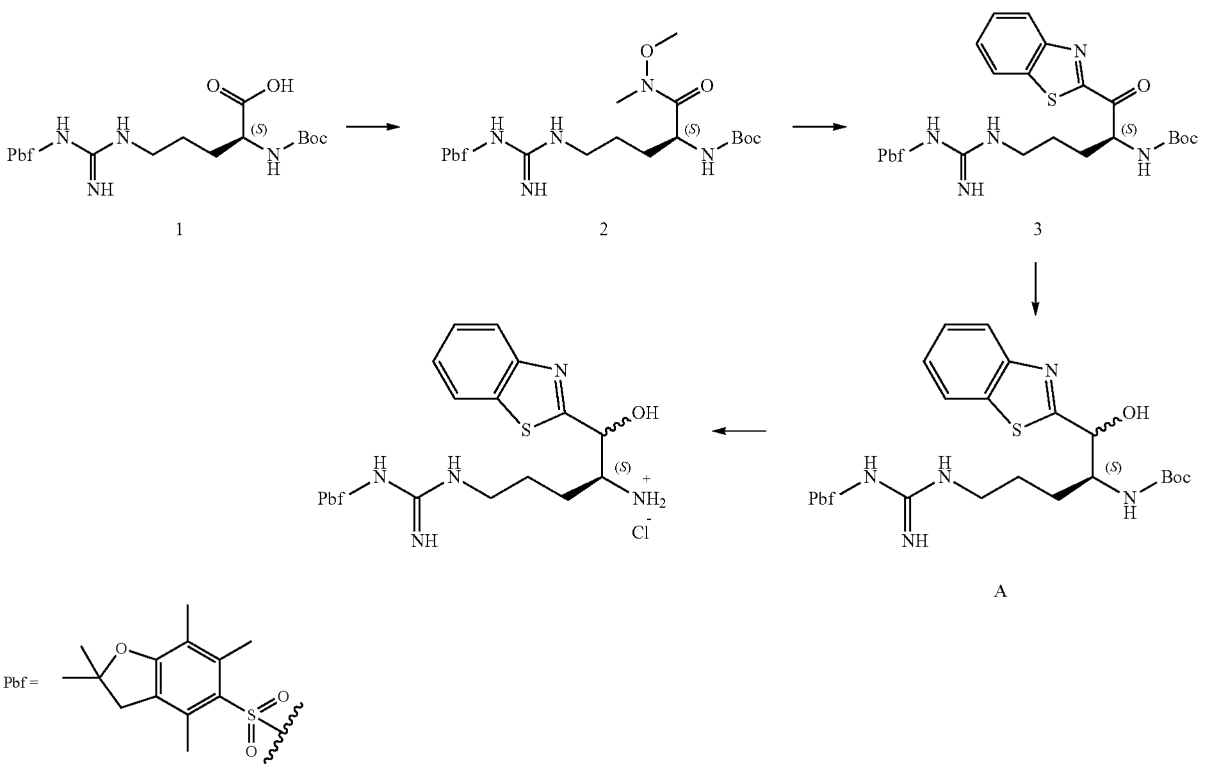

1 2 3 A

Synthesis of Intermediate: 2

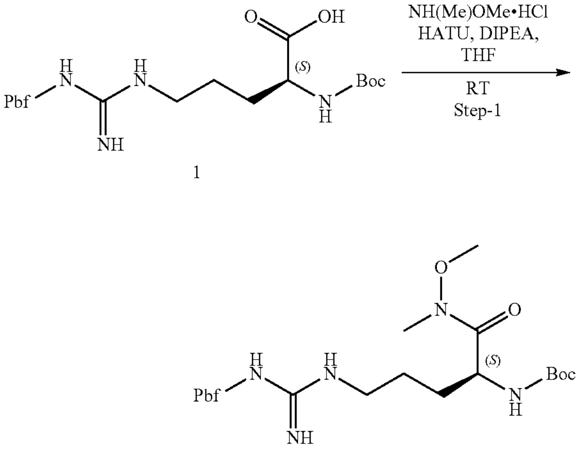

1

2

Procedure

To a stirred solution of Intermediate 1 (35 g, 66.4 mmol) in anhydrous THF (700 mL) was added HATU (37.9 g, 99.6 mmol), N,O-dimethylhydroxylamine.HCl (7.77 g, 79.7 mmol) and DIPEA (35.7 mL, 199.3 mmol) at room temperature and the reaction mixture was allowed to stir overnight. The solvent was evaporated and the crude material was purified by column chromatography using silica gel, eluting with 60-65% ethyl acetate in hexanes. The pure product fractions were collected to afford 35 g of pure product as a white solid in 92% yield. Chiral HPLC purity: 98.88%, $MH^+$569.72

Synthesis of Intermediate: 3

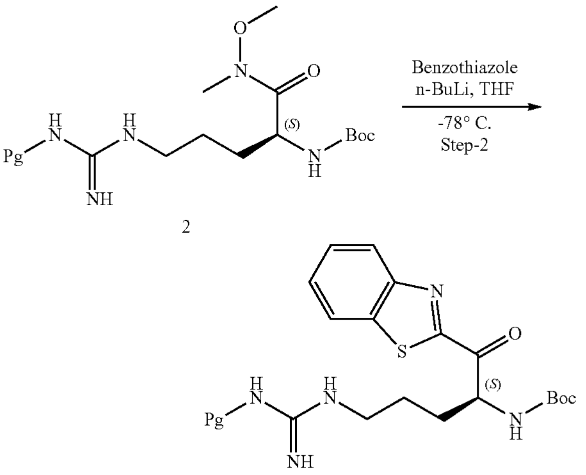

2

3

Procedure

To a stirred solution of benzothiazole (21 mL, 189.56 mmol) in anhydrous THF (125 mL) was added n-BuLi (1M in hexane) (110 mL, 112.33 mmol) at −78° C. by cannula over a period of 20 minutes and stirred for 30 minutes, followed by the addition of solution of Intermediate 2 (12 g, 21.06 mmol) in anhydrous THF (75 mL) within a minute. After 5 minutes, a saturated solution of ammonium chloride (100 mL) was added and the reaction extracted with ethyl acetate (500 mL×3). The combined the organic layers were washed with brine (100 mL), dried over anhydrous sodium sulphate and evaporated under vacuum to afford the crude product. The crude material was purified by silica gel column chromatography, eluting with 2% methanol in dichloromethane. The pure product fractions were collected and evaporated to afford 6.5 g of pure compound in 48% yield. Chiral HPLC SFC purity: S-isomer (82.09%), R-isomer (16.59%). $MH^+$643.95

Synthesis of intermediate A

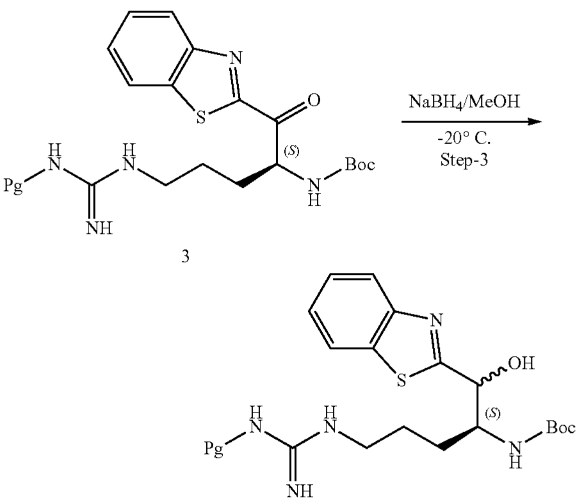

3

A

Procedure

To a stirred solution of Intermediate 3 (13 g, 20.18 mmol) in MeOH (150 mL) at −20° C. was added sodium borohydride (4.58 g, 121.12 mmol) portion wise and stirred for 30 min. After 30 min, acetone (150 mL) was added and the reaction mixture was stirred for 30 minutes. The solvent was evaporated under reduced pressure and water (300 mL) was added to the residue and then extracted with ethyl acetate (500 mL×3). The combined organic layer was washed with brine (500 mL), dried over anhydrous sodium sulphate and evaporated under vacuum to afford the crude product. The crude material was purified by silica gel column chromatography, eluting with 3% methanol in dichloromethane. The pure product fractions were collected and evaporated to afford 9.6 g of pure intermediate A in 74% yield. $^1$H-NMR (DMSO-$d_6$) δ 8.07-8.05 (d, 1H, —ArH), 7.94-7.92 (d, 1H, —ArH), 7.50-7.46 (dd, 1H, —ArH), 7.46-7.38 (dd, 1H, —ArH), 6.79-6.35 (bs, 3H, —NH), 4.86-4.84 (m, 1H, —CH), 3.39 (m, 1H, —CH), 2.95 (bs, 4H, —$CH_2$), 2.49-2.41 (m, 6H, —$CH_3$), 1.99 (s, 3H, —$CH_3$) and 1.44-1.11 (m, 17H, —$CH_2$, —$CH_3$). Chiral HPLC purity (in 4 peaks): 100%, MH+ 645.83.

Example 4: Matriptase Inhibition

Materials

Purified recombinant human matriptase, was prepared as described in Désilets A et. al 2006, Inhibition of human matriptase by eglin c variants. FEBS Lett. April 17; 580(9): 2227-32. Matriptase was active-site titrated with the burst titrant 4-methylumbelliferyl-p-guanidino benzoate (MUGB).

General Kinetic Methods $K_i$ Determination Using Steady-State Velocities

Enzymatic assays and $K_i$ determination were performed at room temperature in an assay buffer containing 50 mM Tris-HCl, 150 mM NaCl and 500 μg/mL BSA at pH 7.4. To determine which method to use for the evaluation of inhibition, 0.25 nM protease was added to a reaction buffer containing 0 nM, 2.5 nM or 1 mM of inhibitors and 200 μM of a fluorogenic substrate (Boc-Gln-Ala-Arg-AMC). Proteolytic activity was monitored by measuring the release of fluorescence (excitation; 360 nm, emission; 441 nm) in a FLX800 TBE microplate reader (Bio-Tek Instruments, Winooski, Vt., USA).

If inhibition occurs only at I/E>10, data generated from plots of enzyme velocity as a function of substrate concentration at several inhibitor concentrations were fitted by nonlinear regression to equations describing different models of reversible inhibition (competitive, uncompetitive, non-competitive and mixed model). The preferred model was used for K determination.

If substantial inhibition occurred using a ratio I/E≤10, compounds were treated as tight-binding inhibitors. Plots of enzyme velocity as a function of inhibitor concentrations were fitted by nonlinear regression analysis to the Morrison equation for $K_i$ determination of tight-binding inhibitors.

All assays were performed at least three times in duplicates, and data were presented as mean±standard error of the mean (SEM). Nonlinear regression and statistical analysis were performed using GraphPad Prism version 6.02 for Windows (GraphPad Software, San Diego, Calif., USA).

Kinetic parameters determination using progress curve analysis

Matriptase cleavage of Boc-Gln-Ala-Arg-AMC was monitored (excitation; 360 nm, emission; 460 nm) 1200 min using a FLX-800 TBE microplate reader (Bio-Tek Instruments, Winooski, Vt., USA).

Equations representing one- and two-step mechanisms of reaction were used to fit the data from the progress curves obtained in the presence of different inhibitor concentrations. Data fitting was performed using Dynafit version 4.07.066.

When rapid equilibrium was assumed, the ON rates for ES and EI formation ($k_1$ and $k_3$) were fixed at 100 $\mu M^{-1}$ $s^{-1}$, and $k_2$ at 8,400 $s^{-1}$ for matriptase to satisfy experimental $K_m$ value. Calculated $K_{cat}$ was fixed to 9.52 $s^{-1}$.

Enzyme inactivation rate ($k_{IE}$) and enzyme concentration ([E]) were determined by curve fitting in the absence of inhibitor when fixing substrate concentration ([S]). Determined values were used as fixed values to determine $k_3$, $k_4$, $k_5$ and $k_6$ values with kinetics in presence of inhibitors. Inhibitor concentrations ([I]) were fitted except for the lowest concentration that was fixed.

For the two-step model, the inhibition constants were calculated as: $K_i=k_4/k_3$, $K_i^*=K_i\ k_6/(k_5+k_6)$, $k_{on}=k_5$ and $k_{off}=k_4\ k_6/(k_4+k_5+k_6)$ The dissociation half-life of the enzyme-inhibitor complex was calculated as $t_{1/2}=0.693/k_{off}$. For the one-step model, $k_{on}$ and $k_{off}$ were equal to $k_3$ and $k_4$, respectively.

The results are shown in Table 1.

Example 5: Cellular Assay-Influenza Virus Replication PR8 and X31 in Calu-3 Human Bronchial Epithelial Cells The ability of the tested compound to block influenza virus replication (PR8 and X31) in Calu-3 human bronchial epithelial cells was evaluated as described by Beaulieu A. et al. J Virol. 2013 April; 87(8):4237-51.

Calu-3 cells were washed with Dulbecco's phosphate-buffered saline (D-PBS) and exposed to influenza virus (diluted in incomplete medium; 0.2% bovine serum albumin [BSA] instead of FBS). After virus adsorption (1 h at 37°

C.), cells were washed once with D-PBS, and cells were incubated in incomplete culture medium containing increasing concentrations of the tested compound for 48 h.

Viral titers were determined in the supernatants of infected cells by viral plaque assays as described by Cloutier et al. J Infect Dis. 2012 Feb. 15; 205(4):621-30. Serial 10-fold dilutions of clarified supernatants were prepared in incomplete Eagle's minimal essential medium (EMEM) (containing 0.1% bovine serum albumin instead of fetal bovine serum) and were titered on Madin-Darby canine kidney (MDCK) cells according to standard viral plaque assays. Confluent MDCK cells were exposed to lung supernatant dilutions for 1 hour to allow virus adsorption. Cells were then washed, and a semifluid medium containing Avicel RC-581 (FMC BioPolymer), incomplete EMEM, and 1 μg/mL Tosyl phenylalanyl chloromethyl ketone (TPCK)-treated trypsin (Sigma-Aldrich) was added to the cells. Cells were incubated for 48 hours, and viral plaques were revealed with 2% crystal violet after Carnoy fixation.

The data shows that the tested compound inhibited PR8 H1N1 and X31 H3N2 influenza virus replication in a dose dependent manner. The results are shown in Table 1.

TABLE 1

| Tested compound | Structure | Matriptase Ki (avg) nM | calu3_pr8_H1N1 $EC_{50}$ (avg) nM | calu3_x31_H3N2 $EC_{50}$ (avg) nM |
|---|---|---|---|---|
| Comparative #1 | 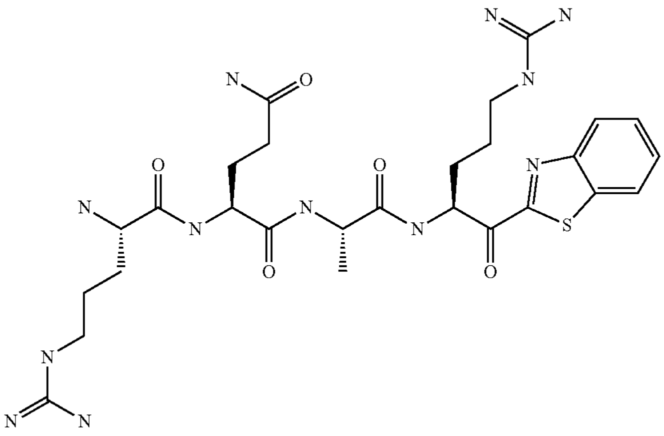 [SMILES: C[C@H](NC(=O)[C@H](CCC(N)=O)NC(=O)[C@@H](N)CCCNC(=N)N)C(=O)N[C@@H](CCCNC(=N)N)C(=O)c1nc2ccccc2s1] | 0.0114 | 5069.3 | 7698.3 |
| Comparative #2 | 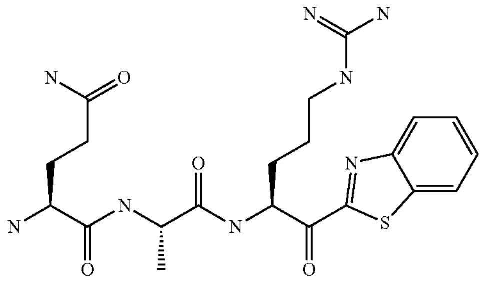 [SMILES: C[C@H](NC(=O)[C@@H](N)CCC(N)=O)C(=O)N[C@@H](CCCNC(=N)N)C(=O)c1nc2ccccc2s1] | 0.0877 | N/A | 5689 |
| Example 1 | 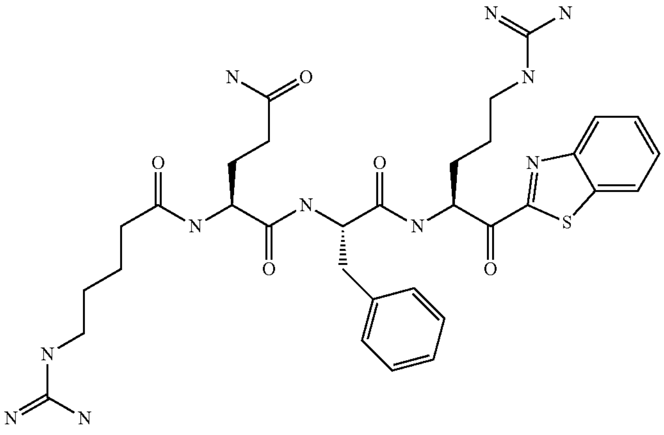 [SMILES: N=C(N)NCCCCC(=O)N[C@@H](CCC(N)=O)C(=O)N[C@@H](Cc1ccccc1)C(=O)N[C@@H](CCCNC(=N)N)C(=O)c1nc2ccccc2s1] | 0.1341 | 27.333 | 20.867 |

TABLE 1-continued

| Tested compound | Structure | Matriptase Ki (avg) nM | calu3_pr8_H1N1 $EC_{50}$ (avg) nM | calu3_x31_H3N2 $EC_{50}$ (avg) nM |
|---|---|---|---|---|
| Example 2 | 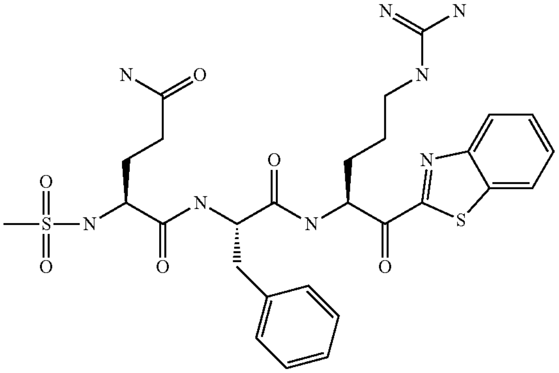 [SMILES: CS(=O)(=O)N[C@@H](CCC(N)=O)C(=O)N[C@@H](Cc1ccccc1)C(=O)N[C@@H](CCCNC(=N)N)C(=O)c1nc2ccccc2s1] | 2.6303 | 1.5583 | 9.3333 |
| Example 3 | 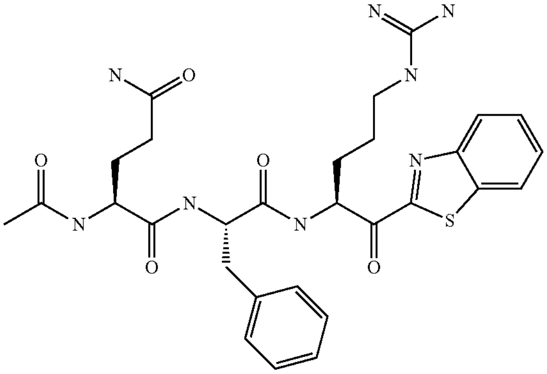 [SMILES: CC(=O)N[C@@H](CCC(N)=O)C(=O)N[C@@H](Cc1ccccc1)C(=O)N[C@@H](CCCNC(=N)N)C(=O)c1nc2ccccc2s1] | 0.5063 | 2.2813 | 34 |

Example 6: Osteoarthritis (OA) Model

The ability of the tested compound to protects against in vivo aggrecan loss in an osteoarthritis (OA) model was evaluated as described by Litherland G J. et al. Arthritis Rheumatol 2014; 66:2175-87.

OA was induced in C57BL/6J mice following destabilization of the medial meniscus (DMM) surgery. Mice received 5 microlitre intraarticular injections of either saline or Compound 1 (10 mg/ml in saline) on days 7 and 28 post surgery. At day 56 post-surgery, mice were killed, knee joints isolated and fixed overnight in 7% formaldehyde in PBS. Joints were decalcified in EDTA in PBS for 10 days and then wax embedded. Consecutive sections (6 μm) were stained with safranin 0 with hematoxylin counterstaining and then cartilage damage graded (by two blinded, independent observers) according to a published grading system [Litherland, 2014]: 0 (normal) to 6 (vertical clefts/erosion to the calcified cartilage extending to 0.75% of the articular surface). Bars show the mean+/−SD of the highestscores in the medial tibial and femoral condyles for each joint. Compound 1 decreased the cartilage damage score. The results are depicted in FIG. 1.

P<0.01 for the control and *P<0.001 for Compound 1, by Kruskal-Wallis test with Dunn's multiple comparison test.

Example 7: Bleomycin-Induced Pulmonary Fibrosis (IPF) Model

Idiopathic Pulmonary Fibrosis (IPF) is a chronic progressive and usually fatal lung disease with no identifiable etiology. Evolving fibrotic process is responsible for an Interstitial Lung Diseases, with abnormal pulmonary functions; including evidence of restriction and impaired gas exchange.

The activity of the compounds of formula I, II or III in IPF is evaluated as follows.

Bleomycin (0.08 U/kg) or PBS is instilled intratracheally into male C57/BL6 mice. Mice are treated intranasally with a tested compound (5 mg/kg/day) starting either the next day after bleomycin instillation (tested compound d1-d10, pre-treatment) or 10 days after bleomycin instillation (tested compound d10-d20, treatment). In both experimental settings (pre-treatment or treatment), saline control groups are included. At day 21 after bleomycin instillation, mice are euthanized and their lungs are harvested. The right lobe is fixed with 10% neutral buffered formalin for 24 hours, transferred to 70% ethanol, and embedded in parafin. Five-micrometer sections are processed for histopathology with Masson's trichrome stain. Fibrosis is quantified using the modified Ashcroft scoring system. n=1, 4-6 mice per group.

The invention claimed is:

1. A compound of formula:

(I)

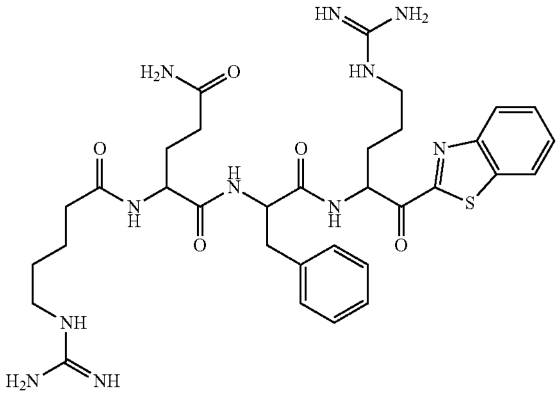

;

(II)

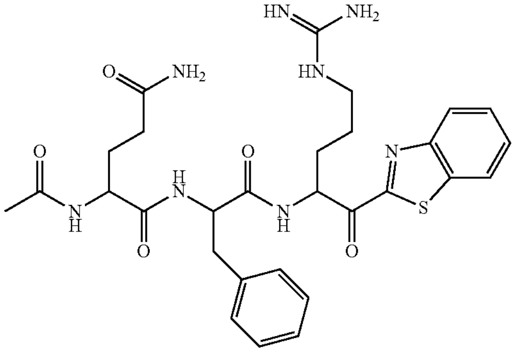

or (III)

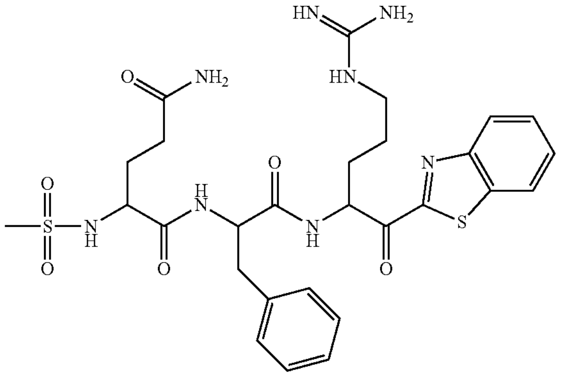

or a pharmaceutically acceptable salt thereof.

2. The compound of claim 1, wherein said compound is of formula:

(I)

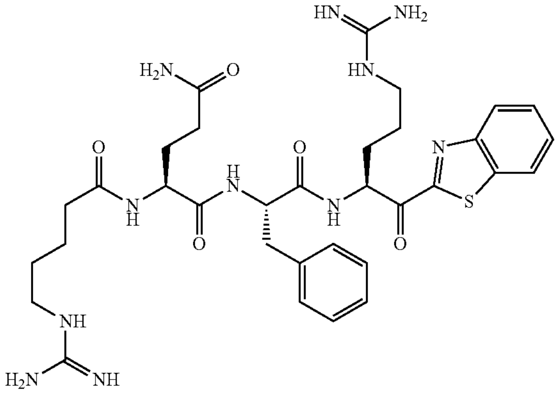

;

(II)

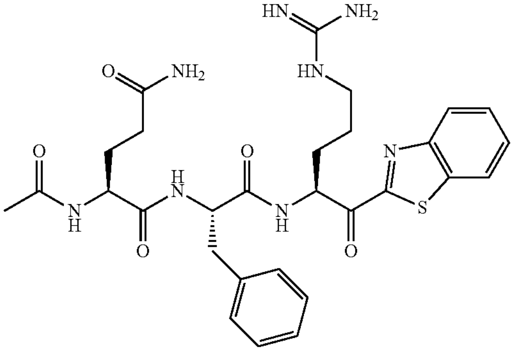

or (III)

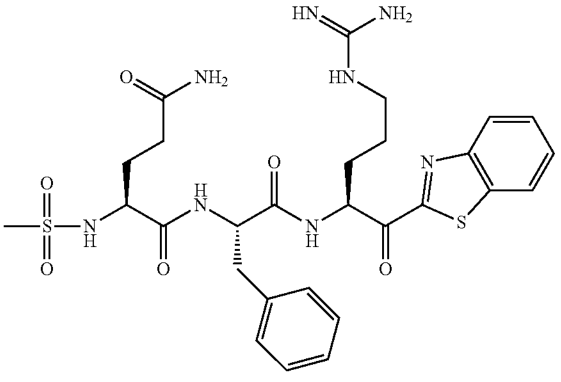

or a pharmaceutically acceptable salt thereof.

3. The compound of claim 1, wherein said compound is formula:

(I)

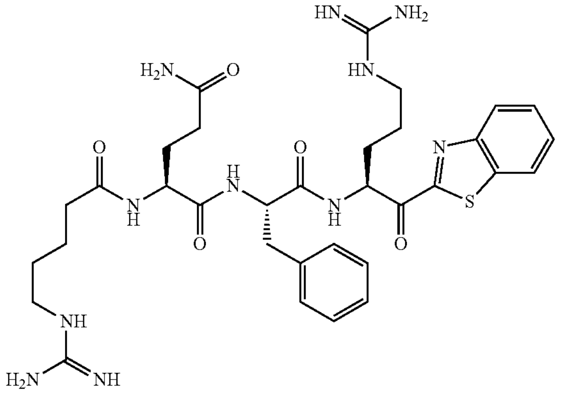

or a pharmaceutically acceptable salt thereof.

4. The compound of claim 1, wherein said compound is formula:

(II)

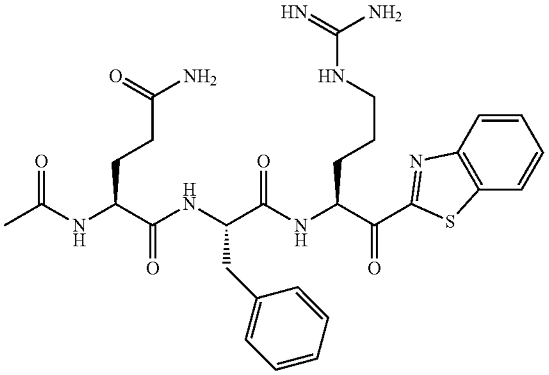

or a pharmaceutically acceptable salt thereof.

5. The compound of claim 1, wherein said compound is formula:

(III)

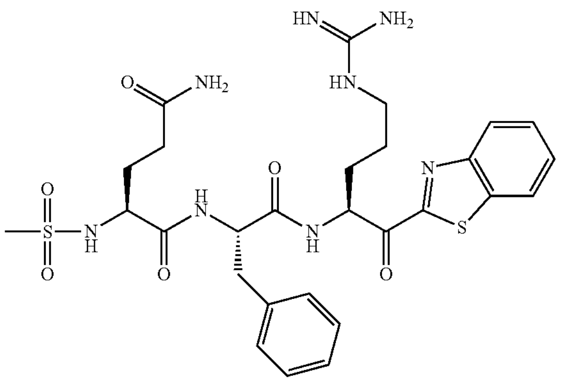

or a pharmaceutically acceptable salt thereof.

6. A pharmaceutical composition comprising a compound according to claim 1 and a pharmaceutically acceptable carrier, diluent and excipient.

7. A method for treating oral squamous cell carcinoma, inflammatory disorders, respiratory disorders, viral infections or disorders associated with iron overload in a subject in need thereof which comprises administering a therapeutically effective amount of a compound according to claim 1 or a composition comprising said compound.

8. The method according to claim 7, for the treatment of oral squamous cell carcinoma.

9. The method according to claim 7, for the treatment of osteoarthritis.

10. The method according to claim 7, for the treatment of idiopathic pulmonary fibrosis.

11. The method according to claim 7, for the treatment of influenza type A, B or C.

12. The method according to claim 7, for the treatment of coronaviruses infections.

13. The method according to claim 7, for the treatment of human coronavirus HCoV-NL63, HCoV-OC43, HCoV-229E, HCoV-HKUI, SARS-CoV (Severe Acute Respiratory Syndrome-Corona Virus), or CoV MERS (Middle East Respiratory Syndrome virus.

14. The method according to claim 7, for the treatment of parainfluenza viruses infections.

15. The method according to claim 7, for the treatment of HPIV type 1, HPIV type 2, HPIV type 3 or HPIV type 4.

16. The method according to claim 7, wherein the subject is a human subject.

17. The method according to claim 7, wherein said compound is of formula:

(I)

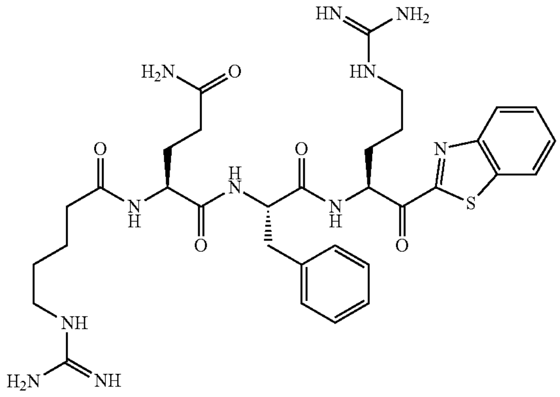

;

(II)

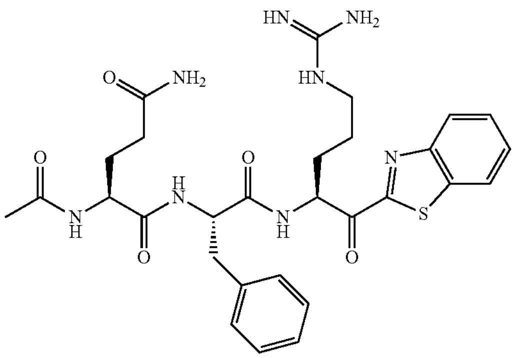

or

-continued
(III)
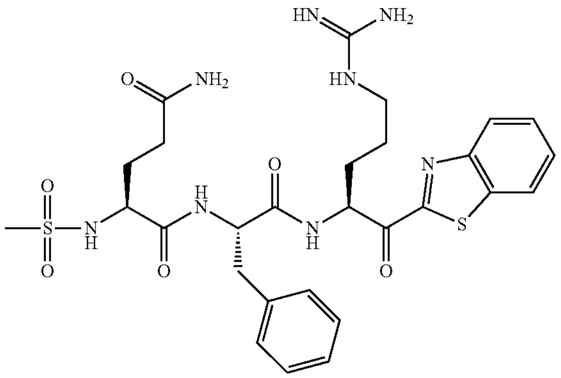
or a pharmaceutically acceptable salt thereof.
18. The method of claim 17, for the treatment of oral squamous cell carcinoma in a human subject.
19. The method of claim 17, for the treatment of osteoarthritis in a human subject.
20. The method of claim 17, for the treatment of idiopathic pulmonary fibrosis in a human subject.
* * * * *